(12) United States Patent  (10) Patent No.: US 8,706,208 B2
Chiao et al.  (45) Date of Patent: Apr. 22, 2014

(54) PASSIVE WIRELESS GASTROESOPHAGEAL SENSOR

(75) Inventors: Jung-Chih Chiao, Grand Prairie, TX (US); Thermpon Ativanichayaphong, Valencia, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 1301 days.

(21) Appl. No.: 12/054,378

(22) Filed: Mar. 24, 2008

(65) Prior Publication Data

US 2008/0234599 A1   Sep. 25, 2008

Related U.S. Application Data

(60) Provisional application No. 60/896,912, filed on Mar. 24, 2007.

(51) Int. Cl.
*A61B 5/05* (2006.01)
*A61B 5/04* (2006.01)
*A61B 5/103* (2006.01)
*A61B 5/117* (2006.01)

(52) U.S. Cl.
USPC ........... 600/547; 600/350; 600/361; 600/380; 600/593

(58) Field of Classification Search
USPC .......................... 600/350, 361, 380, 547, 593
See application file for complete search history.

(56) References Cited

U.S. PATENT DOCUMENTS

| 5,415,181 | A | 5/1995 | Hogrefe et al. |
| 5,833,625 | A | 11/1998 | Essen-Moller |
| 6,582,365 | B1 | 6/2003 | Hines et al. |
| 6,951,536 | B2 | 10/2005 | Yokoi et al. |
| 7,177,621 | B2 * | 2/2007 | Park et al. ...................... 455/337 |
| 7,224,161 | B2 * | 5/2007 | Honkura et al. ............... 324/249 |
| 7,276,147 | B2 * | 10/2007 | Wilsey ........................... 205/792 |
| 7,796,043 | B2 * | 9/2010 | Euliano et al. ............. 340/573.1 |
| 8,265,758 | B2 * | 9/2012 | Policker et al. .................. 607/40 |
| 2005/0182342 | A1 | 8/2005 | Dinsmoor et al. |
| 2005/0245794 | A1 | 11/2005 | Dinsmoor |

(Continued)

FOREIGN PATENT DOCUMENTS

WO    WO 2007034421 A2 *  3/2007

OTHER PUBLICATIONS

Troyk et al. ("Inductively-coupled power and data link for neural prostheses using a class-E oscillator and FSK modulation," IEEE International Conference Engineering in Medicine and Biology Society, vol. 4, pp. 3376-3379, Sep. 2003).*

(Continued)

*Primary Examiner* — Sean Dougherty
*Assistant Examiner* — Devin Henson
(74) *Attorney, Agent, or Firm* — Parks IP Law LLC; Jennifer P. Medlin, Esq.

(57) ABSTRACT

A passive wireless gastroesophageal sensor includes a LC resonance circuit, two or more electrodes and a passive batteryless Radio Frequency Identification (RFID) circuit connected to the LC resonance circuit and the one or more electrodes. The electrodes are configured to measure an impedance within a gastroesophageal tract. The passive batteryless RFID circuit transmits a frequency modulated signal using the LC resonance circuit that varies between a first frequency corresponding to a non-acid reflux condition and a second frequency corresponding to an acid reflux condition based on the measured impedance in response to a signal received from a detector.

19 Claims, 10 Drawing Sheets

(56) References Cited

U.S. PATENT DOCUMENTS

| | | | |
|---|---|---|---|
| 2006/0116564 A1 | 6/2006 | Mintchev et al. | |
| 2006/0231110 A1 | 10/2006 | Mintchev | |
| 2006/0270940 A1 | 11/2006 | Tsukashima et al. | |
| 2007/0096923 A1* | 5/2007 | Lee et al. | 340/572.8 |
| 2007/0225576 A1* | 9/2007 | Brown et al. | 600/301 |

OTHER PUBLICATIONS

DeHennis et al. ("A Wireless Microsystem for the Remote Sensing of Pressure, Temperature, and Relative Humidity", Journal of Microelectromechanical Systems, vol. 14, No. 1, pp. 12-22, Feb. 2005).*

Haile et al. ("Oscillator Circuits for RTD Temperature Sensors," Application note AN895, Microchip Technology Inc., pp. 1-28, 2004).*

2005 IEEE Standard for Safety Levels with Respect to Human Exposure to Radio Frequency Electromagnetic Fields, 3 kHz to 300 GHz, IEEE Std C95.1, pp. 25, 2006.

Al-Zaben, A., et al., "Effect of esophagus status and catheter configuration on multiple intraluminal impedance measurements," Physiol. Meas., vol. 26, Issue 3, pp. 229-238, 2005.

Ativanichayaphong, T., et al., "A wireless sensor for detecting gastroesophageal reflux," SPIE International Smart Materials, Nano- & Micro-Smart Systems Symposium, Dec. 2006.

Ativanichayaphong, T., et al., "A Simple Wireless Batteryless Sensing Platform for Resistive and Capacitive Sensors," IEEE sensor 2007, pp. 139-142, Oct. 2007.

Castell, D., et al., "Combined multichannel intraluminal impedance and pH-metry: an evolving technique to measure type and proximal extent of gastroesophageal reflux," The American Journal of Medicine, vol. 11(8), pp. 157-159, Dec. 2001.

Chaimanonart, N., et al., "Remote RF powering system for wireless MEMS strain sensors," IEEE Sensors Journal, vol. 6(2), pp. 484-489, Apr. 2006.

Chen, S., et al., "Optimization of inductive RFID technology," IEEE International Symposium on Electronics and the Environment, pp. 82-87, 2001.

Devault, K., et al., "Updated guidelines for diagnosis and treatment for gastroesophageal reflux disease," Am J Gastroenterol., vol. 100, Issue 1, pp. 190-200, 2005.

Faloon, W., "The hidden cancer epidemic," Life Extension Magazine, Feb. 2003.

Ghovanloo, M., et al., "A fully digital frequency shift keying demodulator chip for wireless biomedical implants," IEEE Southwest Symposium on Mixed-Signal Design 2003, pp. 223-227, 2003.

Gonzalez-Guillaumin, J., et al., "Ingestible Capsule for Impedance and pH Monitoring in the Esophagus," IEEE Transactions on Biomedical Engineering, vol. 54(12), pp. 2231-2236, Dec. 2007.

Haile, E., et al., "Oscillator Circuits for RTD Temperature Sensors," Application note AN895, Microchip Technology Inc., pp. 21-22, 2004.

Imam, H et al., "Bolus transit patterns in healthy subjects: a study using simultaneous impedance monitoring, . videoesophagram, and esophageal manometry," Am J physiology-GI, vol. 288, Issue 5, pp. 1000-1006, 2004.

Kahrilas, P., "Surgical therapy for reflux disease," The Journal of the American Medical Association, JAMA., vol. 285(18), pp. 2376-2378, May 2001.

Kawamura, O., et al., "Physical and pH properties of gastroesopharyngeal refluxate: A 24-hour simultaneous Ambulatory Impedance and pH monitoring study," Am J Gastroenterol., vol. 99(6), pp. 1000-1010, Jun. 2004.

Lee, Y., et al., "Passive RFID basics," Application Note AN680, Microchip Technology Inc.

Liu, D., et al., "An analog front-end circuit for ISO/IEC 15693-compatible RFID transponder IC," Journal of Zhejiang University—Science A, vol. 7, No. 10 pp. 765-1771, 2006.

Mattox III, H., et al., "Prolonged ambulatory esophageal pH monitoring in the evaluation of gastroesophageal reflux disease," The American Journal of Medicine, vol. 89, Issue 3, pp. 345-356, 1990.

Moore, W., et al., "Transcutaneous RF-Powered Implantable Minipump Driven by a Class-E Transmitter," IEEE Transactions on Biomedical Engineering, vol. 53(8), pp. 1705-1708, Aug. 2006.

Pandolfino, J., et al., "Ambulatory esophageal pH monitoring using a wireless system," Am J Gastroenterol., vol. 98(4), pp. 740-749, Apr. 2003.

Scarpulla, G., et al., "The Impact of Prolonged pH Measurements on the Diagnosis of Gastroesophageal Reflux Disease: 4-Day Wireless pH Studies," Am J Gastroenterol., vol. 102(12), pp. 2642-2647, Dec. 2007.

Shay, S., R. et al., "Twenty-four hour ambulatory simultaneous impedance and pH monitoring: a multicenter report of normal values from 60 healthy volunteers," Am J Gastroenterol., vol. 99(6), pp. 1037-1043, Jun. 2004.

Sorrells, P., "Optimizing read range in RFID systems," Electronics Design, Strategy, News (EDN), pp. 173-184, Dec. 7, 2000.

Starner, T., et al., "Augmenting a pH medical study with wearable video for treatment of GERD," IEEE Eighth International Symposium on Wearable Computers ISWC 2004, vol. 1 pp. 194-195, 2004.

Troyk: P. et al., "Closed-loop class E transcutaneous power and data link for microimplants," IEEE Transactions on Biomedical Engineering, vol. 39(6), pp. 589-599, Jun. 1992.

Troyk, P.R., et al., "Inductively-coupled power and data link for neural prostheses using a class-E oscillator and FSK modulation," IEEE International Conference Engineering in Medicine and Biology Society, vol. 4, pp. 3376-3379, Sep. 2003.

Tutuian, R., et al., "Combined multichannel intraluminal impedance and manometry clarifies esophageal function abnormalities: study in 350 patients," Am J Gastroenterol., vol. 99, Issue 6, pp. 1011-1019, 2004.

Tutuian, R., et al., "Multichannel intraluminal impedance in esophageal function testing and gastroesophageal reflux monitoring," J Clin Gastroenterol., vol. 37(3), pp. 206-215, Sep. 2003.

Vincent, M., et al., "The reticular pattern as a radiographic sign of the Barrett esophagus: an assessment," Radiology, vol. 153, pp. 333-335, 1984.

Waring, J., et al., "The preoperative evaluation of patients considered for laparoscopic antireflux surgery," Am J Gastroenterol., vol. 90, Issue 1, pp. 35-38, 1995.

Wise, K., et al., "Wireless implantable microsystems: high-density electronic interfaces to the nervous system," Proc. IEEE, vol. 92(1), pp. 76-97, Jan. 2004.

Wu, S.-M., et al., "An ASIC for transponder for radio frequency identification system," Proceedings of the Ninth Annual IEEE International ASIC Conference and Exhibit, pp. 111-114, 1996.

Yamada, T., et al., "Battery-less wireless communication system through human body for in-vivo healthcare chip," IEEE Topical Meeting on Silicon Monolithic Integrated Circuits in RF Systems, pp. 322-325, Sep. 2004.

* cited by examiner

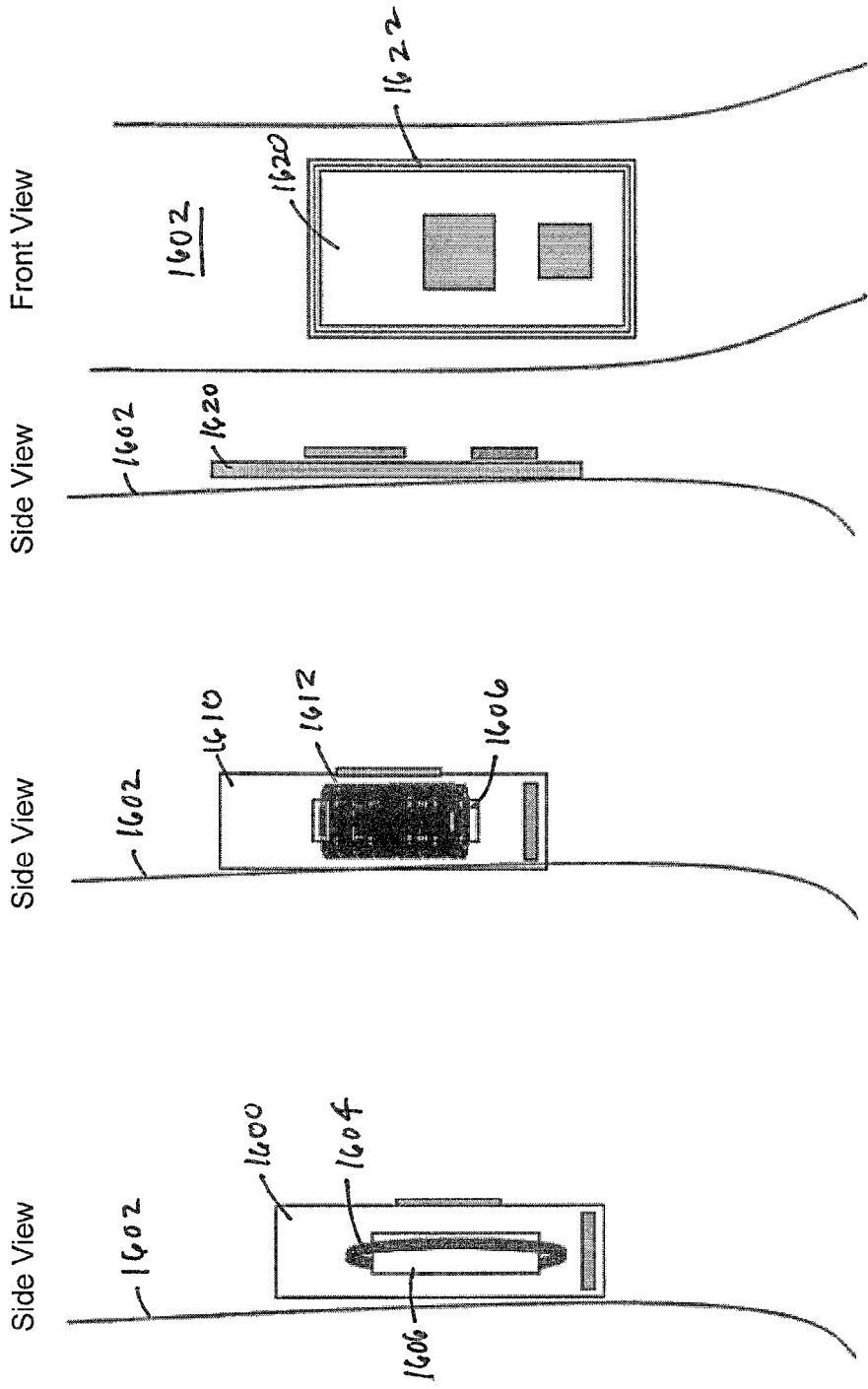

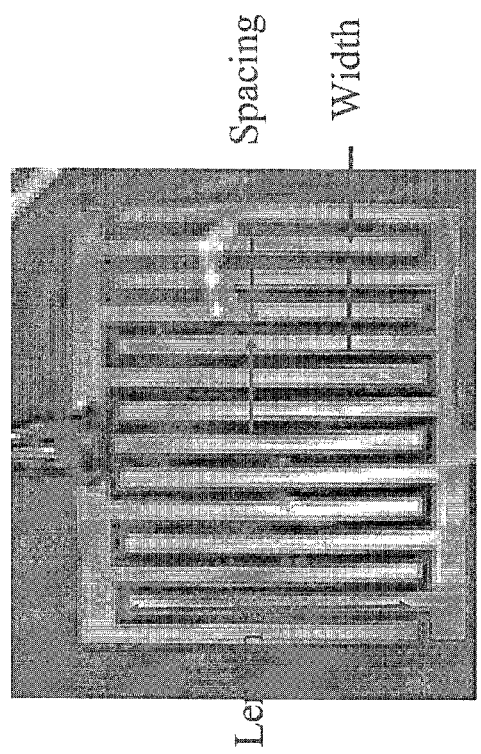
FIGURE 21
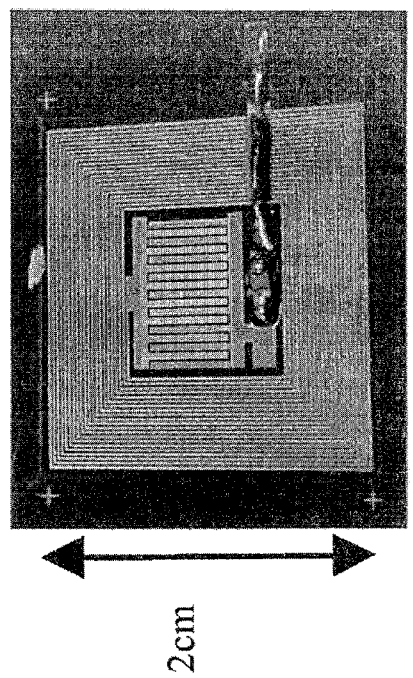
FIGURE 22
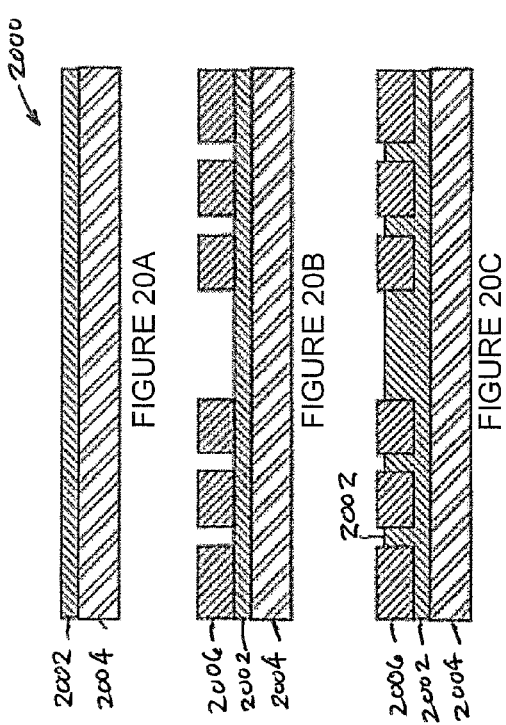
FIGURE 20A
FIGURE 20B
FIGURE 20C
FIGURE 20D
FIGURE 20E
FIGURE 20F

US 8,706,208 B2

PASSIVE WIRELESS GASTROESOPHAGEAL SENSOR

PRIORITY CLAIM TO RELATED APPLICATIONS

This patent application is a non-provisional application of U.S. provisional patent application 60/896,912 filed on Mar. 24, 2007 and entitled "Implantable Wireless RFID Impedance Sensor for Detecting Gastroesopageal Reflux" which is hereby incorporated by reference in its entirety.

FIELD OF THE INVENTION

The present invention relates generally to the field of medical devices and in particular to improved methods of detecting medical conditions such as gastroesophageal reflux through wireless systems.

BACKGROUND OF THE INVENTION

Gastroesophageal reflux disease (GERD) is a medical condition that affects approximately 15% of adult population in the United States and is one of the most prevalent clinical conditions afflicting the gastrointestinal tract. GERD refers to symptoms or tissue damage caused by the reflux of stomach contents into the esophagus and pharynx. The most common symptom of GERD is heartburn and acid regurgitation. GERD has been associated with esophageal cancer and chronic lung damage. Two common esophageal cancers are squamous cell carcinoma and adenocarcinoma. In the United States, esophageal carcinoma accounts for 10,000 to 11,000 deaths per year. Adenocarcinoma of esophagus has the fastest growing incidence rate of all cancers. These increased rates are strongly related to GERD which is the primary risk factor recognized [1]. Therefore, monitoring the GERD symptoms comfortably and reliably becomes more important for early diagnosis of esophageal cancer.

While pH testing has been used to detect acid reflux, esophageal impedance monitoring is a new technique that can detect episodes of gastroesophageal reflux that are both acidic and non-acidic in nature. This technique overcomes the limit of ambulatory pH-metry which does not always reliably detect the reflux of material whose pH value is more than 4.0 [2]. Multichannel intraluminal impedance (MII) probe is a currently available instrument that has been used to correlate symptoms with episodes of gastroesophageal reflux. Whereas electric conductivity is directly related to the ionic concentration of the intraluminal content, materials with high ionic concentrations (e.g. gastric juice or food residues) have relatively low impedance compared with that of the esophageal lining or air [3]. Although the MII probe system brings more accurate monitoring results compared to the conventional pH meter alone, the configuration is bulky and uncomfortable for patients. The tethered sensor probe requires a transnasal insertion procedure and the wire, connecting from the electrodes that stay inside the esophagus to the external electronic unit worn by the patient, stays transnasally for 24 to 48 hours while the patient supposedly resumes normal daily activities. The wired feature limits the clinical utility and accuracy of this technique for protracted monitoring of gastroesophageal reflux. A miniature wireless device that does not require tethered external connections is thus preferred for esophageal reflux monitoring.

To date, a wireless pH monitoring capsule (BRAVO, Medtronic) has been used in some clinical practices [4]. However, it cannot detect non-acid reflux and has a limited battery life. Recent studies and reviews have suggested combined pH and impedance monitoring increased the accuracy of GERD diagnosis [5, 6]. Lately, a combined impedance and pH sensor capsule that could detect both acid and no-acid reflux was developed using a microcontroller and a wireless transmitter [7]. However, the device has limited sampling rates to conserve battery energy. The limited sampling rate may miss reflux episodes between sampling. The limited battery lifetime prohibits the possibility of prolonged measurements that in some clinical cases are needed for increased diagnosis accuracy [8]. Although batteryless wireless approaches for communication of implantable devices have been proposed [9, 10], they are not currently utilized for reflux diagnosis using an impedance to frequency converter.

Accordingly, there remains a need for an improved system that accurately monitors a patient's gastroesophageal acid reflux that is more compact, untethered, improves patient comfort, and does not depend upon an implanted power source for its function.

SUMMARY OF THE INVENTION

The present invention provides an improved system that accurately monitors a patient's gastroesophageal acid reflux that is more compact, untethered, improves patient comfort, and does not depend upon an implanted power source for its function. Moreover, the present invention provides a new method for long term monitoring of gastroesophageal reflux. Based on inductive coupling, the impedance of the reflux can be determined remotely without the need of a battery in the implant. The device includes an energy harvesting circuit, sensing electrodes, an antenna and an impedance to frequency converter. The external reader provides power to the implant and measures the impedance values simultaneously. For example, in one embodiment, a prototype with an overall size of $0.5 \times 1 \times 3$ cm$^3$, was made using a printed circuit board and discrete components. The device was coated with polydimethylsiloxane (PDMS) for implant uses. Experiments were conducted on pig cadavers. The impedance sensor was placed inside the esophagus along with a commercial wireless pH capsule (BRAVO, Medtronic) to compare the performance. The results show good correlation between impedance and pH values of the solutions flushed into the esophagus. Only the impedance sensor can detect non-acid materials, however. The batteryless wireless impedance sensor is able to detect every reflux episode, either acid or non-acid, which will provide more accurate diagnosis of the gastroesophgeal reflux disease (GERD).

A first embodiment of the present invention provides a passive wireless gastroesophageal sensor that includes a LC resonance circuit, two or more electrodes and a passive batteryless Radio Frequency Identification (RFID) circuit connected to the LC resonance circuit and the one or more electrodes. The electrodes are configured to measure an impedance within a gastroesophageal tract. The passive batteryless RFID circuit transmits a frequency modulated signal using the LC resonance circuit that varies between a first frequency corresponding to a non-acid reflux condition and a second frequency corresponding to an acid reflux condition based on the measured impedance in response to a signal received from a detector.

A second embodiment of the present invention provides a system for detecting Gastroesophageal Reflux Disease (GERD) in an animal that includes a detector and one or more sensors. The detector includes an external resonance circuit formed from an external coil, a power amplifier connected to the external resonance circuit, a radio frequency source connected to the power amplifier, an envelope detector connected to the power amplifier, and a band pass filter connected to the envelope detector. The sensor includes a LC resonance circuit, two or more electrodes and a passive batteryless Radio Frequency Identification (RFID) circuit connected to the LC resonance circuit and the one or more electrodes. The electrodes are configured to measure an impedance within a gastroesophageal tract. The passive batteryless RFID circuit transmits a frequency modulated signal using the LC resonance circuit that varies between a first frequency corresponding to a non-acid reflux condition and a second frequency corresponding to an acid reflux condition based on the measured impedance in response to a signal received from the detector.

A third embodiment of the present invention provides a method of wirelessly detecting a refluxate in the gastroesophageal system of an animal by implanting in the gastroesophageal system of the animal an untethered sensor, detecting a transmitted frequency from the sensor using a detector, and determining an acidity of the refluxate based on the detected frequency. The detector includes an external resonance circuit formed from an external coil, a power amplifier connected to the external resonance circuit, a radio frequency source connected to the power amplifier, an envelope detector connected to the power amplifier, and a band pass filter connected to the envelope detector. The sensor includes a LC resonance circuit, two or more electrodes and a passive batteryless Radio Frequency Identification (RFID) circuit connected to the LC resonance circuit and the one or more electrodes. The electrodes are configured to measure an impedance within a gastroesophageal tract. The passive batteryless RFID circuit transmits a frequency modulated signal using the LC resonance circuit that varies between a first frequency corresponding to a non-acid reflux condition and a second frequency corresponding to an acid reflux condition based on the measured impedance in response to a signal received from the detector.

These embodiments and additional embodiments of the present invention are described in detail below with reference to the accompanying drawings.

BRIEF DESCRIPTION OF THE DRAWINGS

The above and further advantages of the invention may be better understood by referring to the following description in conjunction with the accompanying drawings, in which:

FIGS. 16A, 16B and 16C illustrate various antenna configurations in accordance with the present invention;

FIGS. 20A-20F illustrate a method of fabricating the coil and the electrodes using a photolithography processes in accordance with the present invention;

FIG. 21 shows an electrode having interdigitated fingers in accordance with one embodiment of the present invention;

FIG. 22 shows a connector (jumper wire) used to complete the circuit of the coil and the electrodes in accordance with one embodiment of the present invention;

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The present invention provides an improved system that accurately monitors a patient's gastroesophageal acid reflux that is more compact, untethered, improves patient comfort, and does not depend upon an implanted power source for its function. Moreover, the present invention provides a new method for long term monitoring of gastroesophageal reflux. Based on inductive coupling, the impedance of the reflux can be determined remotely without the need of a battery in the implant. The device includes an energy harvesting circuit, sensing electrodes, an antenna and an impedance to frequency converter. The external reader provides power to the implant and measures the impedance values simultaneously. For example, in one embodiment, a prototype with an overall size of 0.5×1×3 cm³, was made using a printed circuit board and discrete components. The device was coated with polydimethylsiloxane (PDMS) for implant uses. Experiments were conducted on pig cadavers. The impedance sensor was placed inside the esophagus along with a commercial wireless pH capsule (BRAVO, Medtronic) to compare the performance. The results show good correlation between impedance and pH values of the solutions flushed into the esophagus. Only the impedance sensor can detect non-acid materials, however. The batteryless wireless impedance sensor is able to detect every reflux episode, either acid or non-acid, which will provide more accurate diagnosis of the gastroesophgeal reflux disease (GERD).

Figure 1:
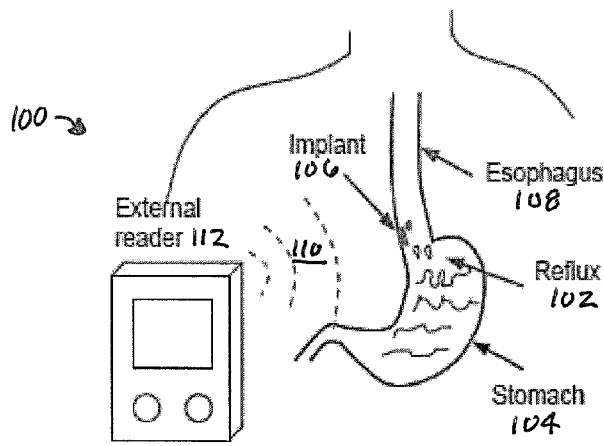
FIG. 1 illustrates a wireless impedance sensor system in accordance with the present invention.

Now referring to FIG. 1, a wireless impedance sensor system 100 in accordance with the present invention is shown. The present invention uses passive telemetry to wirelessly monitor reflux 102 from an animal's stomach 104 using a small passive sensor 106 without a battery that can be attached to the esophagus 108 wall. The implanted sensor 106 harvests radio frequency (RF) powers 110 transmitted from an external reader or detector 112 and transduces impedance variations in the esophagus 108 as RF signals back to the reader 112. As will be further described below, a prototype of the wireless impedance sensor 106 was made and the device was tested in pig cadavers to validate the system functionality.

Figure 2:
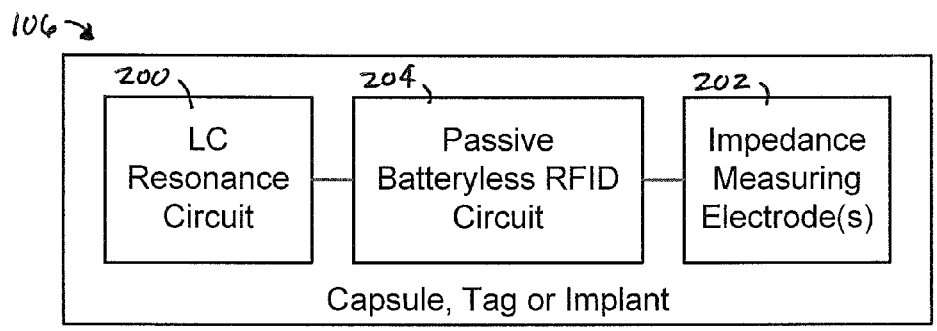
FIG. 2 is a block diagram illustrating a sensor in accordance with the present invention.

Referring now to FIG. 2, a block diagram illustrating a sensor 106 in accordance with the present invention is shown. The passive wireless gastroesophageal sensor 106 includes a LC resonance circuit 200, two or more impedance measuring electrodes 202 and a passive batteryless Radio Frequency Identification (RFID) circuit 204 connected to the LC resonance circuit 200 and the one or more electrodes 202. The electrodes 202 are configured to measure an impedance within a gastroesophageal tract. The passive batteryless RFID circuit 204 transmits a frequency modulated signal using the LC resonance circuit that varies between a first frequency corresponding to a non-acid reflux condition and a second frequency corresponding to an acid reflux condition based on the measured impedance in response to a signal received from a detector. The non-acid reflux condition may include a gas, air, food, drink, saliva or other substance before the substance has entered a stomach disposed on or between the electrodes. The acid reflux condition may include a stomach acid or stomach contents disposed on or between the electrodes. In one example and as illustrated by the test results (FIGS. 12A-12D, 13, 14 and 15), the first frequency can be a measured frequency of between 6 kHz and 11 kHz, and the second frequency can be a measured frequency greater than 11 kHz. The sensor 106 can be configured as a capsule, a tag or an implant.

Figures 3A, 3B:
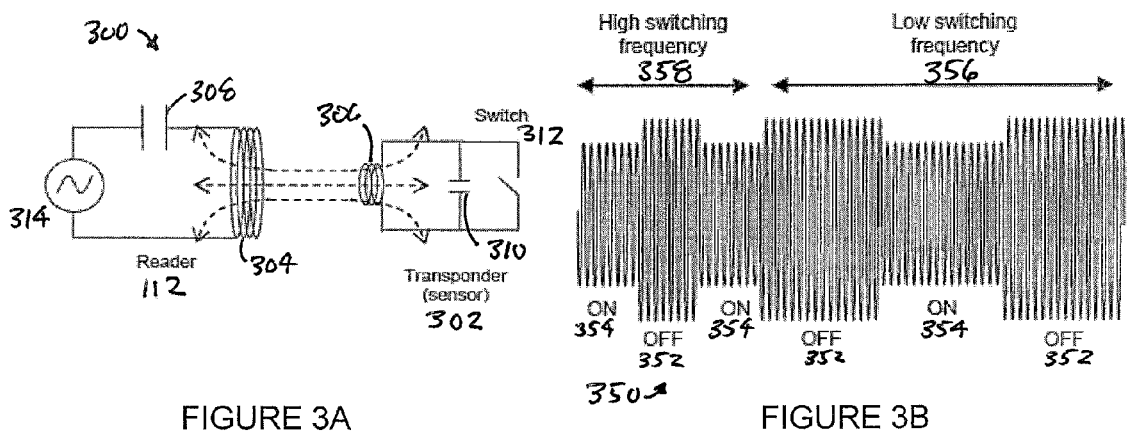
FIG. 3A is a schematic diagram illustrating a basic operating principle of a system in accordance with the present invention.
FIG. 3B illustrates the frequency modulated signals received at the reader coil in accordance with the present invention.

Now referring to FIG. 3A, a schematic diagram illustrating a basic operating principle of a system 300 in accordance with the present invention is shown. Similar to RFID (radio frequency identification) techniques [11], the present invention includes a transponder 302 and a reader 112 in which the communication is based on inductive coupling between two coils 304 and 306. The reader coil 304 generates electromagnetic fields coupling into the transponder coil 306. Each coil 304 and 306 is connected to a capacitor 308 and 310, respectively, forming resonance at the same frequency. In the near field region, the impedance seen by the reader coil 304 changes when the switch 312 at the transponder 302 opens or closes. This load modulation alters the voltage level at the reader coil 304. The variable-frequency source 314 connected to the reader 112 adjusts to the resonant frequency resulting in high amplitude signals at the reader coil 304. The variable frequency is usually much higher than that of the modulating frequency at the transponder 302.

Referring now to FIG. 3B, the frequency modulated signals 350 received at the reader coil 304 in accordance with the present invention are shown. When the switch 312 at the transponder 302 is open (OFF 352), the signal amplitude at the reader 112 is large due to the low loading effect. When the switch 312 is close (ON 354), the transponder 302 loads the reader coil 304 and the reader 112 shifts away from the resonance condition. Thus the signal amplitude is reduced. The switching frequency at the transponder 302 varies with the sensing electrode impedance. When the impedance of refluxant material on the electrode is high, the switch 312 is modulated with a low frequency 356. When the impedance of refluxant material on the electrode is low, the switch 312 is modulated with a high frequency 358. As a result, the transponder 302 switching frequency indicates the measured impedance and can be extracted at the reader 112 using envelope detection. Therefore, a batteryless wireless impedance sensor is achieved.

Figure 4:
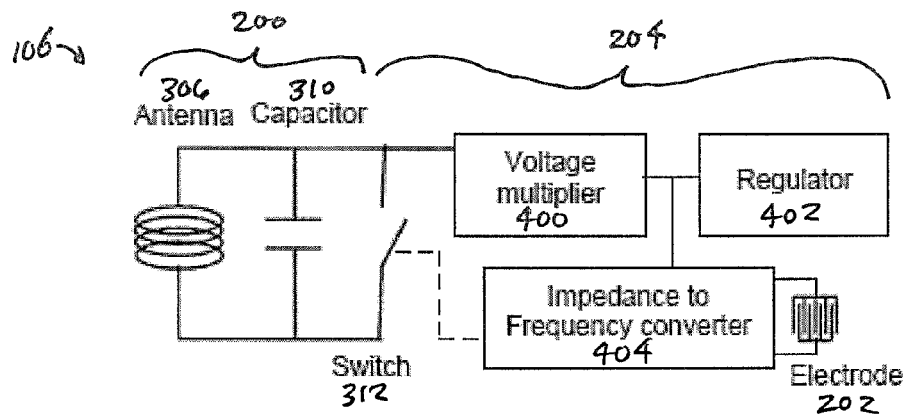
FIG. 4 is a block diagram of a transponder in accordance with one embodiment of the present invention.
Figure 5:
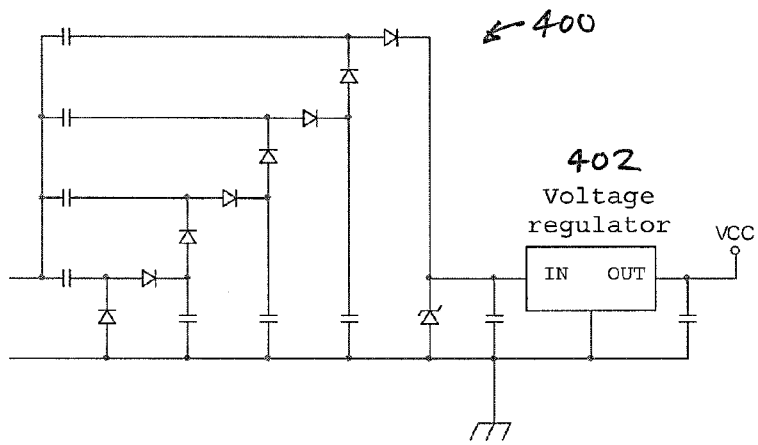
FIG. 5 is a circuit diagram of a voltage multiplier and voltage regulator in accordance with one embodiment of the present invention.

Now referring to FIG. 4, a block diagram of a transponder (sensor) 106 in accordance with one embodiment of the present invention is shown [12]. The front end is a parallel connected antenna 306 and a capacitor 310 forming a LC resonance circuit 200 to receive RF powers from the reader 112. The passive batteryless RFID circuit 204 includes a voltage multiplier 400, a voltage regulator 402, an impedance to frequency converter 404 and a transistor switch 312. The voltage multiplier 400 is connected to the voltage regulator 402. The transistor switch 312 is connected in parallel between the LC resonance circuit 200 and the voltage multiplier 400. The impedance to frequency converter 404 is connected the electrodes 202 and the voltage regulator 402. The impedance to frequency converter 404 controls the transistor switch 312. The voltage multiplier 400 consists of a series of diodes and capacitors (FIG. 5), and increases received RF signals from hundreds of millivolts to volts. The voltage regulator 402 keeps the DC level constant for biasing the circuits. The impedance to frequency converter 404 converts the impedance of electrode 202 to frequency-varying signals. An interdigitated electrode 202 is selected because of its sensitivity to impedance changes. In one example, the electrode 202 contains 6 fingers that are 0.07-mil long, 0.007-mil wide and with a 0.007-mil spacing.

Figure 6:
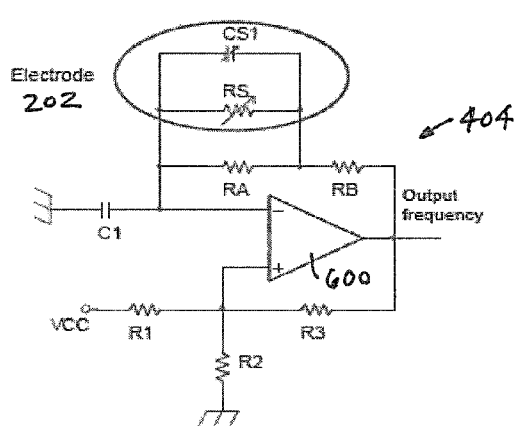
FIG. 6 is a circuit diagram of an impedance-to-frequency converter and electrodes in accordance with one embodiment of the present invention.

Referring now to FIG. 6, a circuit diagram of an impedance-to-frequency converter 404 and electrodes 202 in accordance with one embodiment of the present invention is shown. A relaxation oscillator circuitry was selected, which consists of a comparator 600, a capacitor C1 and several resistors R1, R2, R3, RA and RB. The output frequency of the oscillator is reversely proportional to the time constant at the inverting input and can be calculated from the resistance and capacitance values in the circuit [13]. The electrode 202 is represented by a variable resistor RS and a variable capacitor CS in parallel. The material with low impedance such as acid has low resistance and high capacitance resulting in a high-frequency output. For high impedance material such as air, the resistance is high and the capacitance is low resulting in a low-frequency output.

Figure 7:
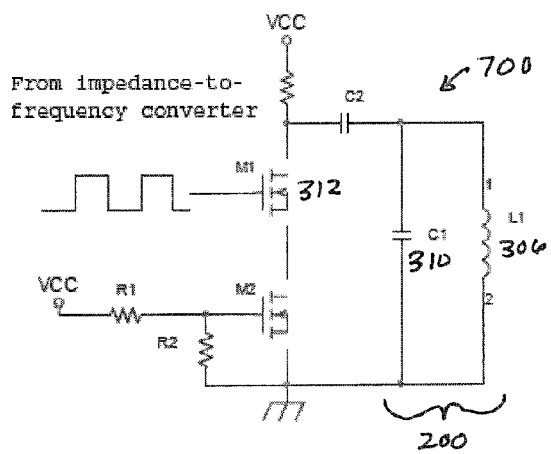
FIG. 7 is a circuit diagram of a modulation circuit in accordance with one embodiment of the present invention.

Now referring to FIG. 7, a circuit diagram of a modulation circuit 700 in accordance with one embodiment of the present invention is shown. To modulate the data back to the reader, the signal is connected to the gate of a MOSFET M1, where Vcc is the regulated DC voltage. L1 and C1 are the transponder antenna 306 and the resonance capacitor 310, respectively. It is important that the modulation must begin after Vcc reaches the regulated voltage. This will keep the output of the impedance-to-frequency converter 404 stable. Moreover, when the modulation occurs, more energy is required to build up the DC voltage. If the modulation begins at a low voltage, the read range of the reader 112 will be reduced dramatically.

To prevent this problem, the transistor M2 is placed at the source of M1. It will be turned on only when Vcc reaches the regulated value. The resistors R1 and R2 are added to form a voltage divider converting the Vcc level to the threshold voltage of M2. When M2 is turned on, M1 behaves as a switch 312 turned on and off by the signals from the impedance-to-frequency generator 404. When M1 is off, L1 and C1 resonate at the same frequency as that of the reader 112. When M1 is on, the capacitor C2 is connected to C1 in parallel. This shifts the resonance frequency of the LC resonant circuit 200 on the transponder 106 resulting in a variation of signal amplitude at the reader 112.

Figure 8:
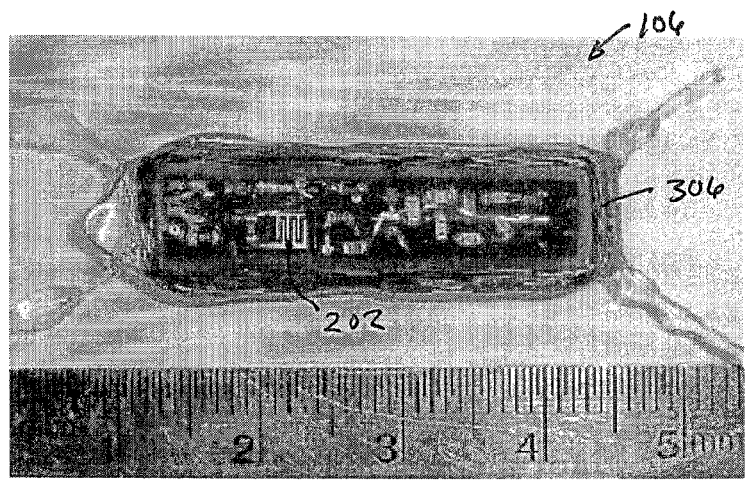
FIG. 8 is an image of a batteryless wireless impedance sensor prototype in accordance with one embodiment of the present invention.

Referring now to FIG. 8, an image of a batteryless wireless impedance sensor 106 prototype in accordance with one embodiment of the present invention is shown. The prototype was made on a 4-layer printed circuit board (PCB) with a size of 0.5×1×3 cm$^3$ and discrete components. If needed, the device size can be further reduced using smaller surface mounted (SMD) components. A coil antenna 306 of 22 µH was made from a 32AWG magnet wire wound around the PCB. When connected to a capacitor 310 of 680 pF, the calculated resonant frequency was 1.3 MHz. The board was then coated with polydimethylsiloxane (PDMS) to prevent short circuit when placed in the esophagus. A small window exposes the sensing electrode 202 to make contact with the refluxant.

Figure 9:
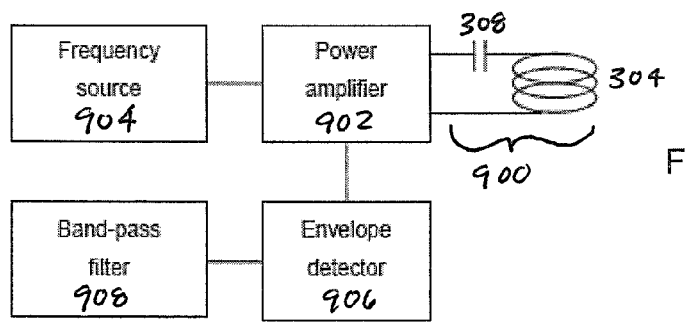
FIG. 9 is a block diagram of a reader in accordance with one embodiment of the present invention.

Now referring to FIG. 9, a block diagram of a reader or detector 112 in accordance with one embodiment of the present invention is shown. The detector 112 includes an external resonance circuit 900 formed from an external coil 304, a power amplifier 902 connected to the external resonance circuit 900, a radio frequency source 904 connected to the power amplifier 902, an envelope detector 906 connected to the power amplifier 902, and a band pass filter 908 connected to the envelope detector 906. The power amplifier 902 generates high electromagnetic fields coupling into the transponder 302. The envelope detector 906 reads the load modulation signals. A frequency source 904 provides carrier signals feeding to the amplifier 902. The source 904 is adjusted to the resonant frequency of the LC circuit resulting in a high voltage at the reader coil 304. When modulation occurs, the voltage level at the reader coil 304 varies. The signal is extracted by the envelope detector 906 and fed through a band-pass filter 908 to suppress the high frequency carrier. Then the frequency-shifted signal is amplified and processed.

Because biological systems attenuate RF signals at higher carrier frequencies, carrier frequencies below 10 MHz may be used over distances of a few centimeters and a carrier frequency of 1.02 MHz was designed for this example. The external coil 304 may be fabricated on any printed circuit board (PCB) having consistent mechanical properties regardless of the dielectric constant selected, and a preferred PCB is the Rogers RO3003 (Rogers Corp., Chandler, Ariz.). The PCB of one embodiment was selected with a dielectric constant of 3.0 and a copper thickness of 35 µm and having a PCB thickness of 1.52 mm. For example, a planar rectangular coil may have 20 turns with a 300-µm width and a 200-µm spacing and an outer perimeters of 6 cm×6 cm. The calculated inductance is 38 µH while the measured inductance is 47.32 µH. Any discrepancy may be due to the undercut etch of the thick copper foil of the PCB, which can easily reduce the conductor width by 70 µm. A capacitance of 330 pF was chosen and connected to the coil in series. In one study, the measured resonance frequency was 1.02 MHz with a quality factor (Q) of around 7, and in another experience the resonance frequency was 850 kHz.

Figure 10:
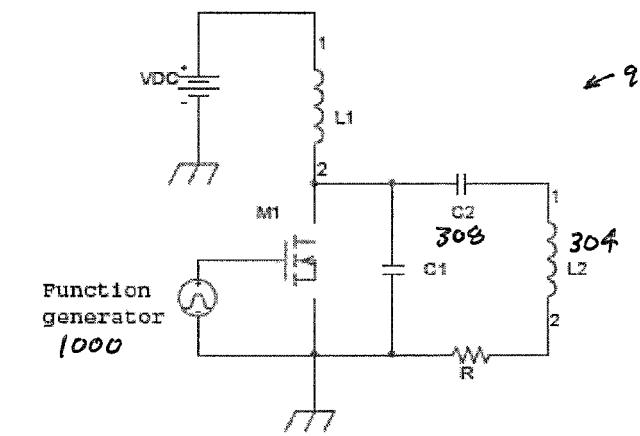
FIG. 10 is a circuit diagram of a class-E power amplifier in accordance with one embodiment of the present invention.

Referring now to FIG. 10, a circuit diagram of a class-E power amplifier 902 in accordance with one embodiment of the present invention is shown. The class-E power amplifier 902 was chosen for its high efficiency. Similar class-E power amplifiers 902 have been considered in transcutaneous power transfer for many previous works [14-16]. A function generator 1000 provides 0-5V square wave signals to drive the MOSFET switch M1. IRL510A was chosen due to its low threshold voltage. A duty-cycle of 30% was chosen to minimize DC power consumption which would eventually be provided by batteries in the portable reader. The design was based on the operating frequency around 1.34 MHz where the recommended maximum permissible exposure (MPE) of magnetic fields is the highest in the frequency ranges from 1.34 MHz to 30 MHz [17]. The operating frequency could be changed according to safety issues, performance and the allowed frequency bands. A coil antenna 304 with a size of 12×15 cm2 was made from an AWG26 magnet wire wound around a frame resulting in an inductance of 17 µH and a high quality Q of 70. Following the calculation procedures for a high quality factor Q approximation in [18], the values of C1 and C2 were chosen to be 10 nF and 900 pF, respectively.

Figure 11:
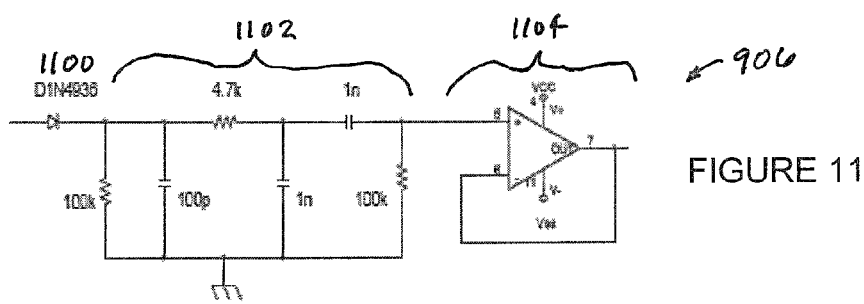
FIG. 11 is a circuit diagram of an envelope detector circuit in accordance with one embodiment of the present invention.

Now referring to FIG. 11, a circuit diagram of an envelope detector 906 circuit in accordance with one embodiment of the present invention is shown. The envelope detector 906 includes a diode 1100 and RC networks 1102. The diode 1N4936 (1100) was chosen to rectify the high voltages at the coil antenna 304 of the class-E amplifier 902. The time constant of the 100-kΩ resistor and 100-pF capacitor gives a modulation frequency of 0.1 MHz that is suitable for a carrier frequency above 1 MHz. The 4.7-kΩ resistor and 1-nF capacitor suppress the high-amplitudes of the high-frequency carrier signals. The 1-nF capacitor and 100-kΩ resistor form a low-pass filter to reduce the DC level before the signals are fed to an op-amp buffer 1104. A bandpass filter 908 was made to read the data from the transponder in the 6-12 kHz bandwidth using op-amps. The signals were then amplified and displayed on a spectrum analyzer.

The optimization of read range for inductive coupling RFID has been discussed in [19]. Briefly referring back to FIG. 3A, the transponder 302 must receive sufficient RF powers from the reader 112 in order to operate properly. The reader 112, on the other hand, must have enough sensitivity to extract the signals from the transponder 302. The read range thus depends on the noise level in the environment as well. In general, using higher electrical currents at the reader 112, using a larger antenna 304 for the reader 112, making lower power sensor circuitry and/or enlarging the transponder antenna 306 will enable the system to satisfy power requirement at a longer distance. Making a high-Q transponder antenna 306 improves the power coupling efficiency but suffers from significant amplitude drops due to frequency shifts that may be caused by manufacturing tolerance of components. In a similar manner, although a high-Q reader antenna 304 improves reader sensitivity, it is also subjected to noises in the environment increasing the possibility of a wrong reading. The prototype in this work was optimized for a read range around 10 cm with reasonable power consumption at the reader. The system was also tested to be able to read the signals from the transponder 302 in liquid environment.

Figure 12B:
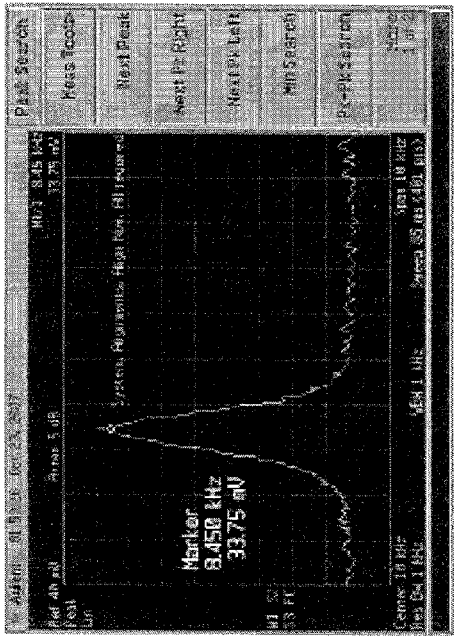
FIGS. 12A-12D are graphs of detected signals from the impedance sensor displayed in a spectrum analyzer in accordance with one embodiment of the present invention.
Figure 12D:
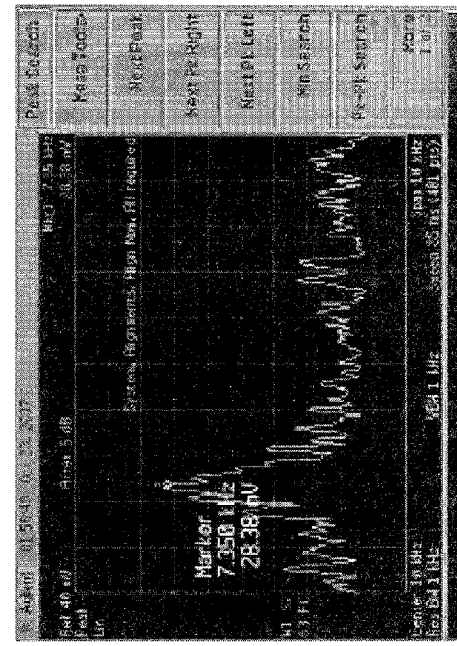
Figure 12A:
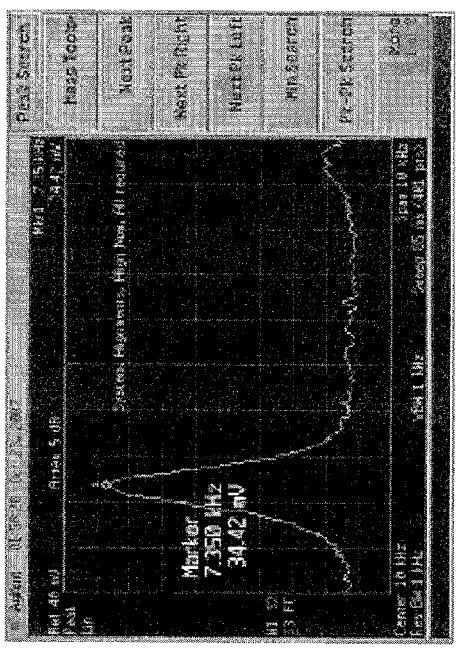
Figure 12C:
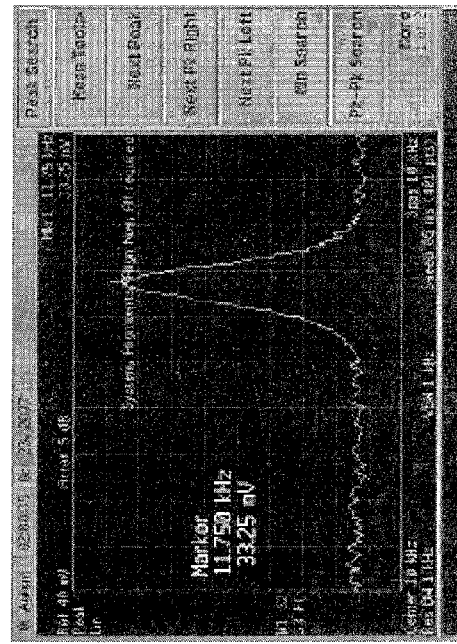

Referring now to FIGS. 12A-12D, graphs of detected signals from the impedance sensor displayed in a spectrum analyzer in accordance with one embodiment of the present invention are shown. The impedance sensor 106 prototype (FIG. 8) was tested in vitro for characterization. It was tested in air, water and acid solutions (diluted HCL). The sensor 106 prototype (FIG. 8) was immersed into the solutions in beakers. The reader antenna 304 was 10 cm away from the sensor 106 and the signals were monitored with a spectrum analyzer. The DC supply at the reader 112 was 8V and 350 mA. The measurement was also done at a 13-cm distance to verify the maximum read range. The materials surrounding the electrode 202 were air (FIG. 12A), water (FIG. 12B) and acid (FIG. 12C) with the reader antenna at a 10-cm distance from the sensor 106. FIG. 12D shows the detected signals at a 13-cm distance when the electrode 202 was surround by air. The measured peak frequency was 7.35 kHz when the impedance sensor 106 was in air (FIG. 12A). When the impedance sensor 106 was immersed in water, the peak frequency increased to 8.45 kHz (FIG. 12B). The measured frequency in acid was 11.75 kHz (FIG. 12C) showing that the acid had very low impedance. The peak frequency was easily observed with large signal-to-noise ratios at a 10-cm distance between the sensor and the reader for all test solutions. The frequency shifts can clearly distinguish air, water and acid solution.

By shaking the transponder inside the beaker mimicking body motion artifacts, the signal quality did not change because the impedance variations were modulated by frequency shifts. The signal attenuation and fluctuations in the carrier did not degrade the modulated sensor signals until the regulated DC voltage Vcc in the transponder drops below 2.5V due to insufficient received energy. The reader 112 was moved farther away from the transponder 302 to test the read range since the inductive power coupling decreased proportionally with the cubic power of the distance [20]. The signal, when measuring the impedance of air, was still readable at a distance of 13 cm (FIG. 12D), but with more noise. Accordingly, the system functions well without errors at a read range of 10 cm.

The prototype of batteryless wireless impedance sensor 106 was compared with a commercial wireless pH capsule (BRAVO, Medtronic). Both sensors were bound together using a suture wire. They together were sequentially immersed in beakers filled with water, orange juice with pulp (OJ(P)), orange juice without pulp (OJ(N)), carbonated diet cola drink (Diet Coke™), vinegar and acid solutions. The sensors were tested again the next day to verify repeatability. After the second day, the BRAVO capsule ran out of battery and stopped working.

To validate our sensors, animal study was conducted in the animal lab at the Southwestern Center for Minimally Invasive Surgery, University of Texas Southwestern. The experiments were performed on three 6-8 months old pig cadavers (75 lbs each). Their average chest perimeter was 70 cm measuring at the level of mid-sternum. The pigs were used in other surgical studies in which the whole GI tract and the chest were intact. The pigs were sacrificed immediately before the start of the impedance sensor experiments. First, an open gastrostomy was created through the anterior gastric wall in the body of the stomach. The gastroscope (Olympus GIF 160) was then advanced into the stomach to remove excessive gastric fluid and content. The sensors were placed in the distal esophagus about 3 cm proximal to the gastroesophageal (GE) junction under direct endoscopic guidance. The measurement of the distance was based on the markings on the shaft of endoscope.

The reader antenna was attached to the pig's skin outside the body around chest. With the transponder in the esophagus, we first tested the motion artifact effects by shaking the pig's body. The sensor signals did not fluctuate. A 16-French nasogastric (NG) tube was advanced through the mouth, larynx and into the mid esophagus for flushing various solutions. The intralumenal location of the NG tube was confirmed by endoscopic visualization. The NG tube was then secured externally to the skin by forceps.

Several solutions were used to test the device performance including diet cola, orange juice, vinegar, salt solution, acid solution and alkaline solution (diluted KOH). Water was flushed in between test solutions to clean the esophagus. A surgical suction tube with continuous suction was placed inside the stomach to remove excessive solution. After each flushing of solution through the esophageal tube, intermittent suction was also applied though the accessory channel of the endoscope to remove excessive fluids in the distal esophagus right below the implant sensors.

The implant location and fluidic activities (solutions of different colors and clarities) were monitored under direct endoscopic visualization. Impedance signals were recorded at different time points corresponding to the flushing of solutions and endoscopic visualization of solution coming around the implants. The pH sensor (BRAVO device) results were compared with the readings from our wireless impedance sensor. The impedance sensor reading was observed immediately since the frequency shift occurred as soon as the liquid touched the electrode, while the BRAVO reading delayed until its specific sampling time. The BRAVO sampling rate is one sample every 30 seconds.

Figure 13:
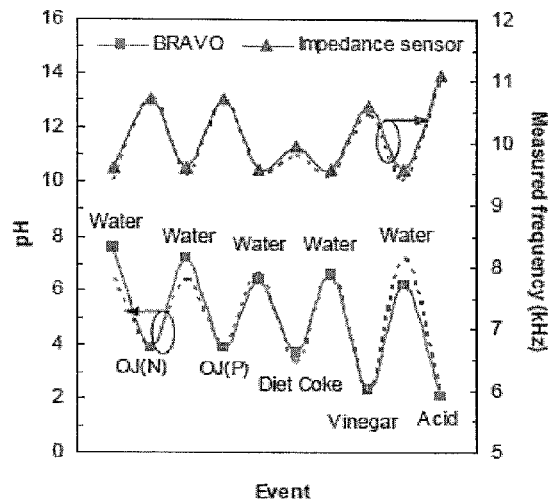
FIG. 13 is a graph illustrating the read frequencies from the impedance sensor in accordance with one embodiment of the present invention and the respective pH values from the BRAVO device.

Now referring to FIG. 13, a graph illustrating the read frequencies from the impedance sensor in accordance with one embodiment of the present invention and the respective pH values from the BRAVO device is shown. The experiments were conducted in beakers. Dash lines indicate the 2nd-day results. Both sensors were tested together twice within 2 days. After the 2nd day, the battery energy of the BRAVO device was exhausted and stopped working while the present invention sensor stayed working. The measured frequencies from the impedance sensor vary between 9 and 11 kHz while the pH values from the BRAVO change from 8 to 2. In general, the measured frequency shifts are correlated with the pH values. The pH changes from low to high corresponding to frequency changes from high to low and vice versa. Orange juice, vinegar, and acid contain significant amounts of ions and produce low impedances. This results in high frequency signals from the impedance sensor. The results from the diet cola, however, were unusual. The diet cola contains carbonic acid with a low pH value and so it has a low impedance. However, during the measurements there were bubbles generated from the drink and accumulated on the electrode. The air bubbles occupied the surface area of the electrode on the impedance sensor preventing the solution to make a good electrical contact with the electrode. The measured frequency for the carbonated cola drink was therefore lower than expected.

Figure 14:
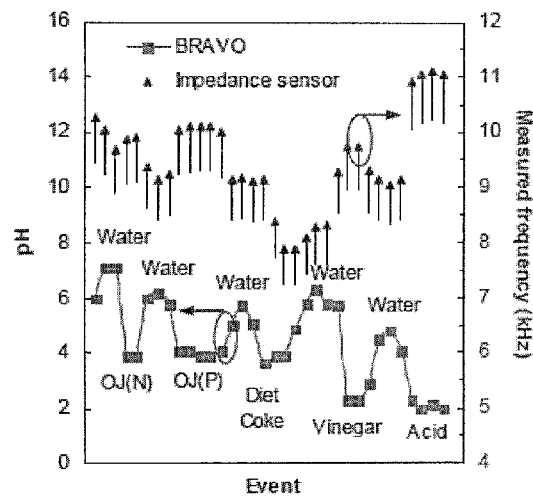
FIG. 14 is a graph illustrating the measured frequencies from the impedance sensor in accordance with one embodiment of the present invention and pH values from the BRAVO device in a pig's esophagus.

Referring now to FIG. 14, a graph illustrating the measured frequencies from the impedance sensor in accordance with one embodiment of the present invention and pH values from the BRAVO device in a pig's esophagus is shown. The measured frequencies and the pH values were correlated in the same way as the experiments in beakers. When the acid solutions such as orange juice, vinegar, and diluted HCL were flushed into the esophagus, the pH values decreased and the measured frequencies increased. Between flushing events, the frequency from the impedance sensor dropped when the liquid left the electrode. However, the frequency did not go back to the one with air (7.35 kHz) because there was still some liquid residue left on the electrode. The frequency drop amounts were also not the same after every flushing due to unpredictable amounts of residue that might stay on the electrode. The frequency drops however were sufficiently clear to identify every flushing episode. In the meantime, the pH values of the BRAVO device remained the same or in the similar levels. The phenomena of liquid residue left on the electrode causing incomplete frequency drop back to 7.35 kHz was also observed in the pH values of BRAVO. After the acidic liquid flushing events, water flushing was not able to bring the pH values back to 7. This indicates that there was acidic residue on both the impedance and pH electrodes.

The arrow and line of the impedance sensor data indicate that the detected frequency rose from a lower frequency during flushing and reached the peak frequency in the middle of a flushing event. The peak frequency stayed the same during flushing. After the flushing finished, the frequency started to drop. This was observed and verified visually with the endoscopy. During water flushing for cleaning purpose, the impedance sensor still indicated each flushing episode as the frequency increased to local peaks and then decreased while the pH sensor reading remained the same. As mentioned before, the frequency shifts were observed immediately when the liquid passed the sensor. The BRAVO pH sensor readings were recorded with a delay due to the fixed sampling periods in the device. When more than one flushing events happened within 30 seconds, the BRAVO reading remained the same while the impedance sensor still detected frequency shifts. In our experiment, each flushing event was spaced with more than one minute in order to record the BRAVO data. These results verified that the impedance sensor could detect acid refluxes and identify every single episode.

The diet cola event showed the same problem as in the tests done in beakers. A lot of air bubbles were generated during flushing. The sensor thus responded to air bubbles as a high impedance air reflux instead of the carbonic acid in the cola drink. The measured frequency was thus very low. Nevertheless, the phenomena verify that the device can detect small air reflux bubbles while the pH sensor cannot.

Figure 15:
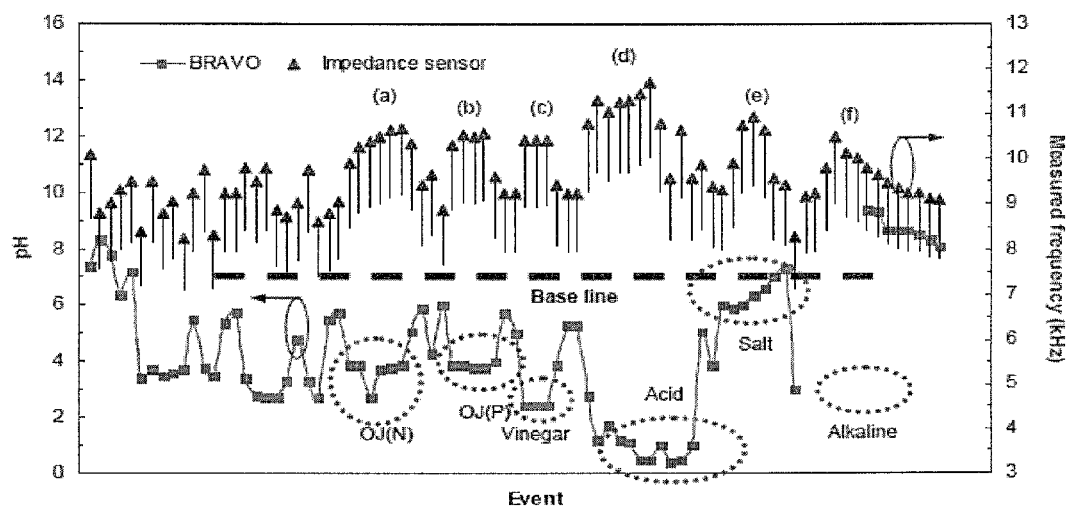
FIG. 15 is a graph illustrating the test results from the impedance sensor in accordance with one embodiment of the present invention and pH values from the BRAVO device in another pig cadaver.

Now referring to FIG. 15, a graph illustrating the test results from the impedance sensor in accordance with one embodiment of the present invention and pH values from the BRAVO device in another pig cadaver is shown. The frequency peaks from the impedance sensor were for (a) OJ(N), (b) OJ(P), (c) vinegar, (d) acid solution, (e) salt solution and (f) alkaline solution, respectively. Water was flushed between the test solutions to clean the electrode. The experimental procedure was the same as before. The data showed that the pH dropped from the base line when there were acid refluxes caused from orange juice without pulp (OJ(N)), orange juice with pulp (OJ(P)), vinegar and acid solutions. The measured frequencies from the impedance sensor increased from the base line accordingly. The frequency peaks are indicated (a) for OJ(N), (b) for OJ(P), (c) for vinegar and (d) for acid solutions, respectively. The impedance and pH sensors showed very high correlation. The results from the salt solution, however, did not significantly change the pH values from the BRAVO capsule to indicate reflux episodes because the pH value of salt solution was close to that of water. The impedance sensor, on the other hand, detected the salt reflux in the same manner of the acid reflux as the frequency increased noticeably from the base line (e). For alkaline reflux, the BRAVO capsule indicated "errors" as the pH was out of the detection range while the impedance sensor gave high frequency results indicating the low impedance of the alkaline solution (f).

The foregoing results demonstrate that an implantable batteryless wireless impedance sensor for gastroesophageal reflux diagnosis has been designed, fabricated and validated. The approach is based on impedance measurement that can detect both acid and non-acid reflux. The wireless device does not require a battery and so there is no time limit for monitoring as in other wireless measurement approaches. The device was tested in pig cadavers demonstrating the feasibility and accuracy of detecting acid and non-acid reflux episodes. The results showed comparable performance to the commercial wireless pH sensors (BRAVO) when detect acid reflux. Furthermore, the impedance sensing method was able to detect non-acid or alkaline reflux episodes as it could distinguish air from water, acid and alkaline solutions. The read range was demonstrated with the reader at a 10-cm distance from the transponder in a beaker and through the pigs' body with an average chest perimeter of 70 cm. The signals were clear without interference of motion artifacts. The transponder prototype was small enough for use in esophagus even it was built with discrete components. Eventually the transponder can be designed with an integrated chip to further reduce implant sizes as those used in RFID tags. The custom designed chip will enable ultra low power consumption and be capable of much longer read ranges.

Other embodiments and design considerations will now be described. For example, FIGS. 16A, 16B and 16C illustrate various antenna configurations in accordance with the present invention. FIG. 16A shows a sensor configured as a capsule 1600 attached to esophagus wall 1602 wherein the antenna is formed by a coil 1604 wrapped lengthwise around a ferrite coil 1606. FIG. 16B shows a sensor configured as a capsule 1610 attached to esophagus wall 1602 wherein the antenna is formed by a coil 1612 wrapped widthwise around a ferrite coil 1606. FIG. 16C (side and front views) shows a sensor configured as a tag 1620 attached to esophagus wall 1602 wherein the antenna is formed by a planar coil 1622 disposed on a flexible substrate that is wrapped along the perimeter of the tag 1620.

Figure 17A:
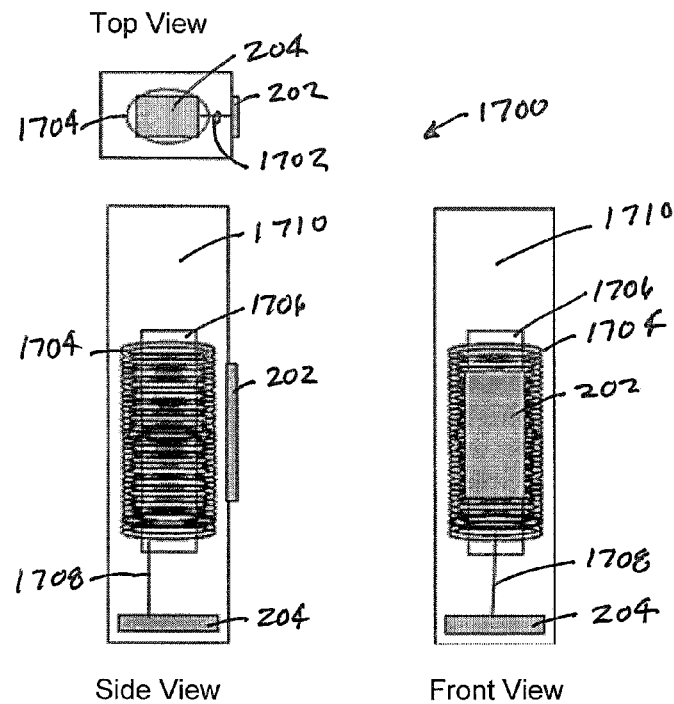
FIGS. 17A and 17B illustrate various packaging configurations in accordance with the present invention.
Figure 17B:
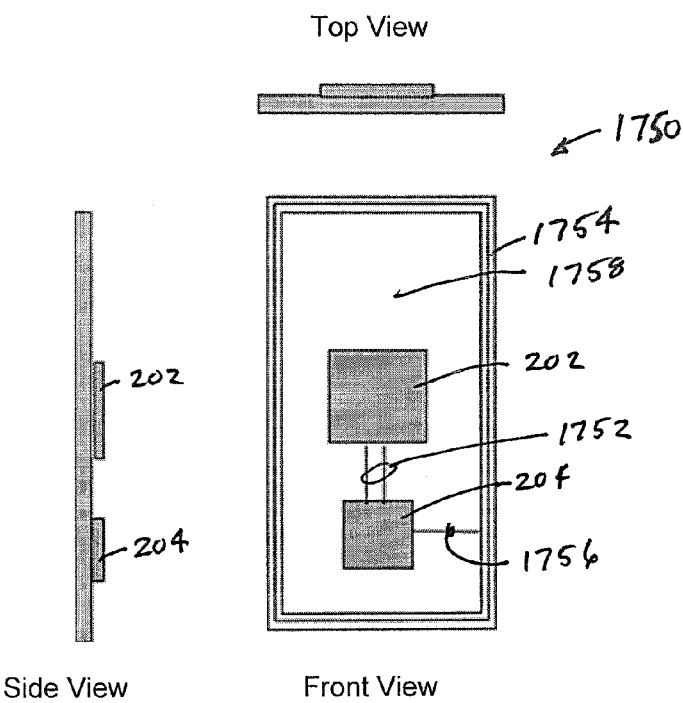

FIGS. 17A and 17B illustrate various packaging configurations in accordance with the present invention. FIG. 17A shows a sensor configured as a capsule 1700 having an impedance sensing electrode 202 and a passive batteryless RFID circuit 204 on a chip connected by wire 1702. The LC resonance circuit 200 includes a coil 1704 wound widthwise around a ferrite core 1706 and connected to the passive batteryless RFID circuit 204 by wire 1708. The capsule 1700 also includes space 1710 for attachment to the esophagus wall. FIG. 17B shows a sensor configured as a tag 1750 having an impedance sensing electrode 202 and a passive batteryless RFID circuit 204 on a chip connected by planar circuitry 1752. The LC resonance circuit 200 includes a planar coil 1754 disposed on a flexible or non-flexible substrate that is wrapped along the perimeter of the tag 1750 and connected to the passive batteryless RFID circuit 204 by wire 1756. The capsule 1700 also includes space 1758 for attachment to the esophagus wall.

Figure 18A:
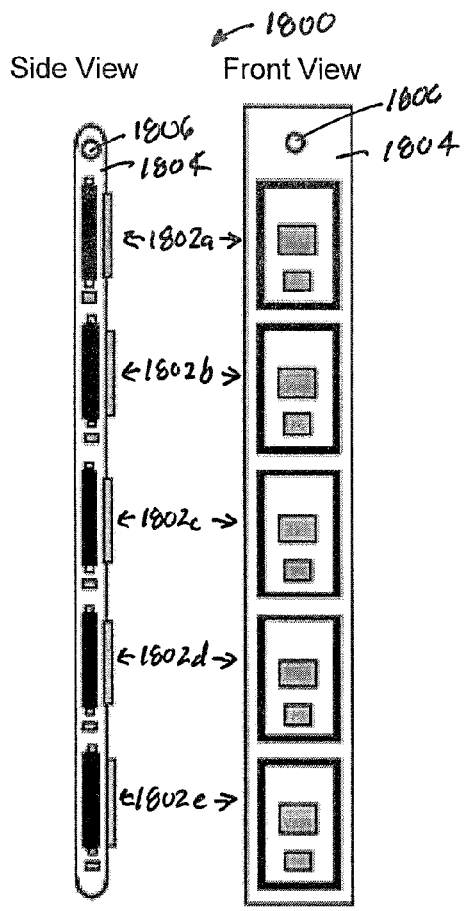
FIGS. 18A and 18B illustrate various array configurations in accordance with the present invention.
Figure 18B:
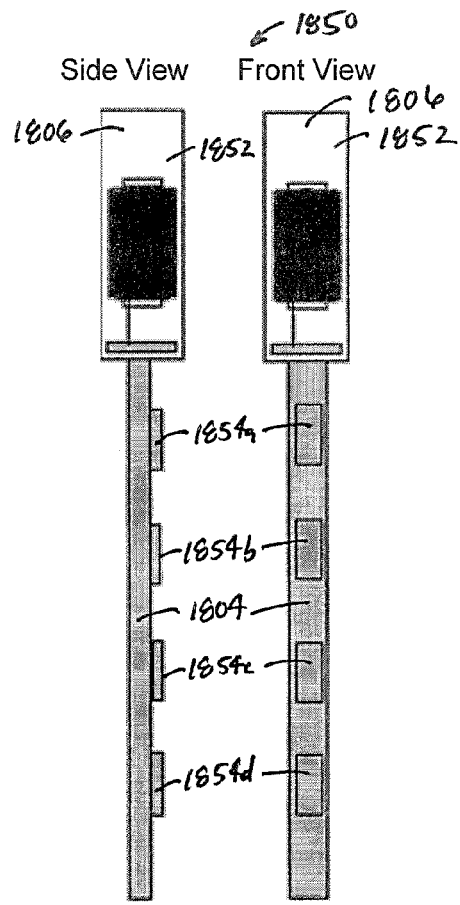

FIGS. 18A and 18B illustrate various array configurations in accordance with the present invention. FIG. 18A shows an array implant configuration 1800 wherein five sensors 1802a, 1802b, 1802c, 1802d and 1802e are attached to, partially encapsulated by, or connected by a biodegradable substrate 1804 that attaches to the esophagus wall at point 1806. The substrate 1804 degrades and breaks apart after approximately 48 hours. The sensors 1802 then pass through the GI tract and are expelled. Each sensor 1802 is on a flexible substrate, has its own resonant frequency and its own RFID to identify location. FIG. 18B shows an array implant configuration 1850 wherein a capsule 1852 is connected to four sensor electrodes 1854a, 1854b, 1854c and 1854d that are attached to, partially encapsulated by, or connected by a biodegradable substrate 1804 that attaches to the esophagus wall at point 1806. The substrate 1804 degrades and breaks apart after approximately 48 hours. The sensors electrodes 1854 then pass through the GI tract and are expelled. The metal also breaks apart and is expelled.

Figure 19:
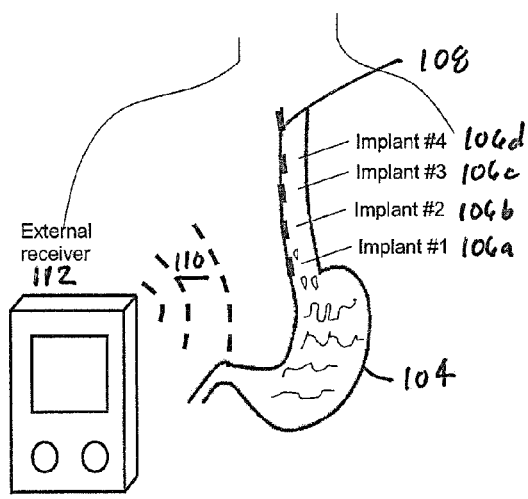
FIG. 19 illustrates a system having multiple wireless impedance sensors in accordance with the present invention.

FIG. 19 illustrates a system having multiple wireless impedance sensors in accordance with the present invention. This embodiment of the present invention uses passive telemetry to wirelessly monitor reflux 102 from an animal's stomach 104 using a multiple small passive sensors 106a, 106b, 106c and 106d without a battery that can be attached to the esophagus 108 wall. The implanted sensors 106a-d harvest radio frequency (RF) powers 110 transmitted from an external reader or detector 112 and transduces impedance variations in the esophagus 108 as RF signals back to the reader 112.

As shown in FIGS. 20A-20F, the coil and the electrodes may be fabricated by a photolithography processes 2000. First, a 2000-Å seed layer 2002 of Cu was thermally evaporated onto a flexible polyimide substrate 2004, such as Kapton® film (DuPont, Wilmington Del.) although any similar flexible substrate is acceptable FIG. 20A. Photoresist 2006 (such as NR7-3000P obtained from Futurex or any suitable photoresist) was spin coated, baked and patterned for the coil and the electrodes mold FIG. 20B. A seed layer of Cr/Cu/Cr or Ti/Cu/Ti can be used for better adhesion of Kapton/Cu and Cu/photoresist interfaces (not shown). The thick photoresist layer was achieved by two layers of NR7-3000P with a spinning speed of 1000 rpm for 30 seconds. The baking temperatures and times of the $1^{st}$ and $2^{nd}$ layers are 120° C./1 min and 150° C./1 min 20 sec, respectively. The sample was exposed to UV light and baked at 120° C. for 70 sec. The baking was done in an oven to evenly heat the photoresist on the non-flat substrate. The sample was put in a Cu electroplating solution for 2 hours with an electrical current of 10 mA. A total Cu layer of about 8 μm was formed, FIG. 20C, to achieve low resistance. The photoresist was removed by putting the sample in an ultrasonic bath with acetone for 10 min and then the Cu layer was etched away, as shown in FIG. 20D. A 10-μm thick layer 2008 of an epoxy-based negative resist (such as SU-8 made by MicroChem, Newton, Mass. however any similar epoxy-based negative resist is suitable) was spun, patterned and then hard cured onto the coil area to prevent undesired electrical contact, as shown in FIG. 20E. The sample was then Ni electroplated 2010 to protect the Cu electrode from corrosion in acid, as shown in FIG. 20F. FIG. 21 shows an electrode 202 having interdigitated fingers that are about 0.4 mm wide and about 5 mm long with about 0.1 mm spacing there between. The sensitivity of the sensor can be adjusted by changing the width, length and spacing of the interdigitated fingers of the electrode.

FIG. 22 shows a connector (jumper wire) used to complete the circuit of the coil and the electrodes. This also can be done by depositing a metal airbridge with first thermal evaporator and then electroplating processes. The coil inductance was measured as 9.41 μH, which is close to the theoretical value of 9.1 μH. The measured DC resistance of the coil is 13Ω resulting in a calculated quality factor (Q) of 4.63 using the equation $Q=\omega L/R$, where ω is the angular frequency. The Q value can be improved by plating a thicker Cu layer to reduce the coil resistance. The capacitance for the resonance frequency at 1.02 MHz was calculated to be 2587 pF. An SMD (surface mount device) capacitor of 2200 pF, the closest value available, was selected and soldered onto the sample. A metal-insulator-metal (MIM) capacitor can be fabricated instead to achieve the exact capacitance in the future without using the hybrid components. Interdigitated electrodes are located in the center of planar coil so that it is in the outer area to maximize the inductance.

To further characterize the preferred structure of the electrode(s) of the impedance sensor in measuring acid refluxate, three electrodes were fabricated to investigate the performance of the interdigitated structures. Each design has the total area of 1×1 cm² with different finger widths and spacings. The capacitances of the electrodes when immersed in air, city water and simulated stomach acid (70:1 and 50:1 muriatic acid) were measured and are shown in Table 1.

TABLE 1

Capacitances of each electrode design in different solutions.

| Conductor width/spacing | 1000 μm/100 μm | 500 μm/50 μm | 250 μm/50 μm |
|---|---|---|---|
| Air | 2.7 pF | 5.3 pF | 9 pF |
| City water | 43 pF | 77 pF | 116 pF |
| Stomach acid (70:1) | >1 μF | >1 μF | >1 μF |
| Stomach acid (50:1) | >1 μF | >1 μF | >1 μF |

Referring to Table 1 (above), the capacitance of the electrodes in air is much lower than in water or acid. The capacitance in acid reaches the μF ranges for all designs, which is much higher than those in air or water. The results show that smaller finger spacing and narrower finger width (which means more fingers) result in higher capacitance for electrodes with the same total area. The dimensions of the electrodes can be adjusted with the parameters in mind to achieve a desired sensitivity for specific impedance measurements.

Additional information regarding the use of FSK modulation will now be described. The device operating with direct modulation (or amplitude modulation) is susceptible to noise, and the relative accuracy will vary with the distance between the tag and reader due to different body types and the body movement of the patient. To mitigate the possibility of noise affecting the impedance signal, frequency shift keying may optionally be used. Frequency Shift Keying (FSK). Frequency shift keying (FSK) provides very high noise immunity. K. Finkenzeller, *RFID Handbook: Fundamentals And Applications In Contactless Smart Cards And Identification*, Chichester, England, New York: Wiley, 2003, and Y. Lee and P. Sorrells, "Passive RFID basics," *Application Note AN*680, Microchip Technology Inc., relevant portions incorporated herein by reference. The FSK signal is less susceptible to the misalignment in coupling coils and artifacts from motion, which are two major problems in biomedical implants.

A FSK system has two operating frequencies that are digitally generated by a series of D flip-flops to divide the carrier frequency from the reader. D. Liu, X. Zou, Q. Yang and T. Xiong, "An analog front-end circuit for ISO/IEC 15693-compatible RFID transponder IC," *Journal of Zhejiang University-Science A*, Vol. 7, No. 10 pp. 765-1771, 2006, herein incorporated by reference. In the present invention, the transmitted impedance signal is analog, which needs to be transmitted instead of the '0' and '1' bits of the FSK signal. The signal is related to the impedance of esophagus measured by the electrodes. The frequency thus needs to vary between f1 and f2 to reflect the impedance ranging between air and acid. To create FSK signals, astable multivibrator circuits are used with the present invention to reduce signal noise, S.-M. Wu, J.-R. Yang and T.-Y. Liu, "An ASIC for transponder for radio frequency identification system," *Proceedings of the Ninth Annual IEEE International ASIC Conference and Exhibit*, pp. 111-114, (1996), herein incorporated by reference. The generated frequency is directly related to a variable capacitor in the circuits, which in the present invention, is the impedance electrodes of the tag.

To verify the feasibility, a study was conducted using a modified commercial timer IC TS555 (STMicroelectronics, Carrollton, Tex.) or any suitable time IC in the astable mode operating at 1.5V, where the capacitor, C, in the connection diagram was replaced by the sensing electrodes of the tag. Table 2 (below) shows the capacitance of electrodes with a finger size of 250 μm wide and 50 μm spacing.

TABLE 2

Capacitance of electrodes in different solutions

| Solution | Capacitance |
| --- | --- |
| Air | 9 pF |
| City water | 116 pF |
| Stomach acid (70:1) | >1 μF |
| Stomach acid (50:1) | >1 μF |

The frequency of the square wave generated by TS555 can be calculated from the equation:

$$f = \frac{1.44}{(R_A + 2R_B)C}$$

The capacitance of the sensing electrodes 44, however, can vary from pF to μF in air and acid, which can make the TS555 IC timer unable to operate in the whole range of the frequency, and moreover, the systems will require very high bandwidth, which is difficult to achieve at both the tag and reader. To keep the capacitance in the desired range, two fixed capacitors C1 and C2 were added.

The series and parallel connection with the additional capacitors keeps the total capacitance in the range of C1 (62) and C2 (64) where C2>>C1. When there was only air on the electrodes, the impedance was high and the total capacitance is close to 1nF resulting in an output frequency of 263 kHz. When acid was dropped onto the electrode, the total capacitance reached 11 nF. Considering the sensing electrodes also measure resistance, the output frequency still varies with respect to the capacitance change. The frequency reduced to 68.5 kHz and 40.5 kHz when water and simulated stomach acid were on the electrodes, respectively.

The integrated RFID chip can be connected to the electrodes and the resonance capacitor by wire bonding. The flip-chip bonding used for conventional RFID tags is suitable for this configuration to reduce parasitics and costs. The tag's antenna, capacitor and the electrode can be fabricated together in a batch fashion using standard photolithography as previously described. The astable multivibrator circuits can be designed together with a traditional RFID circuitry and sensor/ID control. The frequency generated from the astable multivibrator can be used to trigger a transistor connected to the LC resonance circuit on the tag. The sensor modulator includes astable mutivibrator circuits connected to sensing electrodes. The modulator turns the transistor on and off with the frequency corresponding to the measured impedance. This transistor tunes and detunes the LC resonance circuit and creates signal envelope variation at the reader. The impedance value can be extracted by counting the number of high frequency carrier pulses between the edges of the signal envelopes.

As with an individual tag, FSK is also helpful in the array (multiple tag) aspect of the present invention. In the array, a reader reads a first impedance sensor then reads the FSK to determine if there is refluxate in the vicinity of the first sensor. Then the reader or an additional reader interrogates a second impedance sensor and reads FSK to determine if there is refluxate in the vicinity of the second sensor and so on. This array configuration permits a user to predict the flow of the refluxate and take preventative measures before the problem is exacerbated, for instance, before refluxate reaches to the top of the esophagus. In this aspect, the reader (external resonance circuit) may be uniquely coupled to one tag (impedance sensor) or may read a subset of tags, or the entire set of tags.

At the reader, the square waves will be extracted, and the frequency will be calculated from the number of pulses in a certain amount of time, or the sampling period. In practice, the impedance monitoring can be done at 50 samples per second or 20 ms sampling period. In 20 ms, at least 2 pulses must be transmitted from the tag for the correct frequency calculation at the reader. The reading frequency is the number of pulses divided by the sampling period which is the average frequency transmitted from the tag. The minimum frequency requirement of the FSK modulation is thus around 100 Hz. A higher frequency can increase the sampling rate and is less subjected to the distortion from carrier rejection filter which is used in most demodulation circuit at the reader.

The carrier frequencies have a wide range between 100 kHz and 1 MHz depending on practical considerations. A lower frequency has better penetration through human tissues, however, its shorter propagation range is the tradeoff. The frequency of 125 kHz ISM band is suitable for the FSK our applications since the propagation distance is short. The modulation frequency around $f_c/8$ or $f_c/10$ will allow the sampling rate of several kilohertz, which is more than enough for impedance monitoring.

Figure 23:
FIG. 23 shows a sensor disposed on a flexible substrate in accordance with one embodiment of the present invention.
Figure 24:
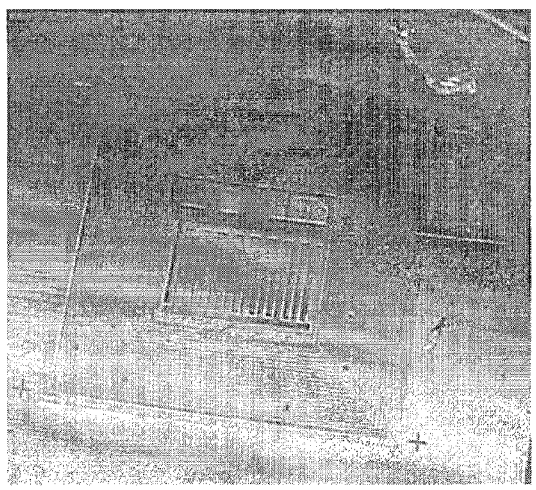
FIG. 24 shows a sensor configured for use in a tag in accordance with one embodiment of the present invention.

FIG. 23 shows a sensor disposed on a flexible substrate in accordance with one embodiment of the present invention. FIG. 24 shows a sensor configured for use in a tag in accordance with one embodiment of the present invention. Additional information and test results can be found the provisional patent application identified above and in the inventor's previously published articles and papers listed below as References [12,30,36,37], which are hereby incorporated by reference in their entirety.

It is contemplated that any embodiment discussed in this specification can be implemented with respect to any apparatus, method, kit or system of the invention, and vice versa. Furthermore, compositions of the invention can be used to achieve methods of the invention. It will be understood that particular embodiments described herein are shown by way of illustration and not as limitations of the invention.

The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the following claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

REFERENCES

[1] P. Kahrilas, "Surgical therapy for reflux disease," *The Journal of the American Medical Association, JAMA.*, Vol. 285(18), pp. 2376-2378, May 2001.

[2] S. Shay, R. Tutuian, D. Sifrim, M. Vela, J. Wise, N. Balaji, X. Zhang, T. Adhami, J. Murray, J. Peters and D. Castell, "Twenty-four hour ambulatory simultaneous impedance and pH monitoring: a multicenter report of normal values from 60 healthy volunteers," *Am J Gastroenterol.*, Vol. 99(6), pp. 1037-1043, June 2004.

[3] R. Tutuian, M. Vela, S. Shay and D. Castell, "Multichannel intraluminal impedance in esophageal function testing and gastroesophageal reflux monitoring," *J Clin Gastroenterol.*, Vol. 37(3), pp. 206-215, September 2003.

[4] J. Pandolfino, J. Richter, T. Ours, J. Guardino, J. Chapman and P. Kahrilas, "Ambulatory esophageal pH monitoring using a wireless system," *Am J Gastroenterol.*, Vol. 98(4), pp. 740-749, April 2003.

[5] O. Kawamura, M. Aslam, T. Rittmann, C. Hofmann and R. Shaker, "Physical and pH properties of gastroesophargeal refluxate: A 24-hour simultaneous Ambulatory Impedance and pH monitoring study," *Am J Gastroenterol.*, Vol. 99(6), pp. 1000-1010, June 2004.

[6] D. Castell and M. Vela, "Combined multichannel intraluminal impedance and pH-metry: an evolving technique to measure type and proximal extent of gastroesophageal reflux," *The American Journal of Medicine*, Vol. 11(8), pp. 157-159, December 2001.

[7] J. Gonzalez-Guillaumin, D. Sadowski, K. Kaler and M. Mintchev, "Ingestible Capsule for Impedance and pH Monitoring in the Esophagus," *IEEE Transactions on Biomedical Engineering*, Vol. 54(12), pp. 2231-2236, December 2007.

[8] G. Scarpulla, S. Camilleri, P. Galante, M. Manganaro and M. Fox, "The Impact of Prolonged pH Measurements on the Diagnosis of Gastroesophageal Reflux Disease: 4-Day Wireless pH Studies," *Am J Gastroenterol.*, Vol. 102(12), pp. 2642-2647, December 2007.

[9] W. Moore, D. Holschneider, T. Givrad and J.-M. I. Maarek, "Transcutaneous RF-Powered Implantable Minipump Driven by a Class-E Transmitter," *IEEE Transactions on Biomedical Engineering*, Vol. 53(8), pp. 1705-1708, August 2006.

[10] T. Yamada, T. Uezono, H. Sugawara, K. Okada, K. Masu, A. Oki and Y. Horiike, "Battery-less wireless communication system through human body for in-vivo healthcare chip," *IEEE Topical Meeting on Silicon Monolithic Integrated Circuits in RF Systems*, pp. 322-325, September 2004.

[11] K. Finkenzeller, *RFID handbook: fundamentals and applications in contactless smart cards and identification*, Chichester, England, New York, Wiley, Chapter 3, pp. 41-47, 2003.

[12] T. Ativanichayaphong, J. Wang, W. Huang, S. Rao and J. C. Chiao, "A Simple Wireless Batteryless Sensing Platform for Resistive and Capacitive Sensors," *IEEE sensor 2007*, pp. 139-142, October 2007.

[13] E. Haile and J. Lepkowski, *Oscillator Circuits for RTD Temperature Sensors, Application note AN895*, Microchip Technology Inc., pp. 21-22, 2004.

[14] K. Wise, D. Anderson, J. Hetke, D. Kipke, K. Najafi, "Wireless implantable microsystems: high-density electronic interfaces to the nervous system," *Proc. IEEE*, Vol. 92(1), pp. 76-97, January 2004.

[15] P. R. Troyk and G. A. DeMichele, "Inductively-coupled power and data link for neural prostheses using a class-E oscillator and FSK modulation," *IEEE International Conference Engineering in Medicine and Biology Society*, Vol. 4, pp. 3376-3379, September 2003.

[16] N. Chaimanonart, D. J. Young, "Remote RF powering system for wireless MEMS strain sensors," *IEEE Sensors Journal*, Vol. 6(2), pp. 484-489, April 2006.

[17] 2005 IEEE Standard for Safety Levels with Respect to Human Exposure to Radio Frequency Electromagnetic Fields, 3 kHz to 300 GHz, IEEE Std C95.1, pp. 25, 2006.

[18] P. Troyk, and M. Schwan, "Closed-loop class E transcutaneous power and data link for microimplants," *IEEE Transactions on Biomedical Engineering*, Vol. 39(6), pp. 589-599, June 1992.

[19] P. Sorrells, "Optimizing read range in RFID systems," Electronics Design, Strategy, News (EDN), pp. 173-184, Dec. 7, 2000.

[20] S. Chen and V. Thomas, "Optimization of inductive RFID technology," *IEEE International Symposium on Electronics and the Environment*, pp. 82-87, 2001

[21] T. Starner and D. Ashbrook, "Augmenting a pH medical study with wearable video for treatment of GERD," *IEEE Eighth International Symposium on Wearable Computers ISWC 2004*, Vol. 1 pp. 194-195, 2004.

[22] W. Faloon, "The hidden cancer epidemic," *Life Extension Magazine*, February 2003.

[23] M. Vincent, A. Robbins, S. Spechler, R. Schwartz, W. Doos and E. Schimmel, "The reticular pattern as a radiographic sign of the Barrett esophagus: an assessment," *Radiology*, Vol. 153, pp. 333-335, 1984.

[24] J. Waring, J. Hunter, M. Oddsdottir, J. Wo, E. Katz, "The preoperative evaluation of patients considered for laparoscopic antireflux surgery," *Am J Gastroenterol.*, Vol. 90, Issue 1, pp. 35-38, 1995.

[25] H. Mattox III and J. Richter, "Prolonged ambulatory esophageal pH monitoring in the evaluation of gastroesophageal reflux disease," *The American Journal of Medicine*, Vol. 89, Issue 3, pp. 345-356, 1990.

[26] K. DeVault and D. Castell, "Updated guidelines for diagnosis and treatment for gastroesophageal reflux disease," *Am J Gastroenterol.*, Vol. 100, Issue 1, pp. 190-200, 2005.

[27] R. Tutuian and D. Castell, "Combined multichannel intraluminal impedance and manometry clarifies esophageal function abnormalities: study in 350 patients," *Am J Gastroenterol.*, Vol. 99, Issue 6, pp. 1011-1019, 2004.

[28] H. Imam, S. Shay, A. Ali and M. Baker, "Bolus transit patterns in healthy subjects: a study using simultaneous impedance monitoring, videoesophagram, and esophageal manometry," *Am J physiology-GI*, Vol. 288, Issue 5, pp. 1000-1006, 2004.

[29] A. Al-Zaben and V. Chandrasekar, "Effect of esophagus status and catheter configuration on multiple intraluminal impedance measurements," *Physiol. Meas.*, Vol. 26, Issue 3, pp. 229-238, 2005.

[30] T. Ativanichayaphong, W.-D. Huang, J. Wang, S. Rao, H. F. Tibbals, S.-J. Tang, S. Spechler, H. Stephanou and J.-C. Chiao, "A wireless sensor for detecting gastroesophageal reflux," *SPIE International Smart Materials, Nano- & Micro-Smart Systems Symposium*, December 2006.

[31] K. Finkenzeller, *RFID handbook: fundamentals and applications in contactless smart cards and identification*, Chichester, England, New York: Wiley, 2003.

[32] Y. Lee and P. Sorrells, "Passive RFID basics," Application Note AN680, Microchip Technology Inc.

[33] M. Ghovanloo and K. Najafi, "A fully digital frequency shift keying demodulator chip for wireless biomedical implants," *IEEE Southwest Symposium on Mixed-Signal Design* 2003, pp. 223-227, 2003.

[34] D. Liu, X. Zou, Q. Yang and T. Xiong, "An analog front-end circuit for ISO/IEC 15693-compatible RFID transponder IC," *Journal of Zhejiang University-Science A*, Vol. 7, No. 10 pp. 765-1771, 2006.

[35] S.-M. Wu, J.-R. Yang and T.-Y. Liu, "An ASIC for transponder for radio frequency identification system," *Proceedings of the Ninth Annual IEEE International ASIC Conference and Exhibit*, pp. 111-114, 1996.

[36] T. Ativanichayaphong, J. Wang, W. D. Huang, S. Rao, H. F. Tibbals, S. J. Tang, S. J. Spechler and J. C. Chiao, "A Wireless Impedance Sensor for Detecting Gastroesophageal Reflux," *BMES Biomedical Engineering Society Annual Meeting*, Los Angeles, Calif., Sep. 26-29, 2007.

[37] Thermpon Ativanichayaphong, Wen-Ding Huang, Jianqun Wang, Smitha M. N. Rao, H. F. Tibbals, Shou-Jiang Tang, Stuart Spechler, Harry Stephanou and J. C. Chiao, "An Implantable Wireless Impedance Sensor Capable of Distinguishing Air, Water and Acid in Gastroesophageal Reflux,", Digestive Disease Week 2007, Washington D.C., May 19-24, 2007.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims.

What is claimed is:

1. A passive wireless gastroesophageal sensor comprising:
an LC (inductor capacitor) resonance circuit;
one or more electrodes configured to measure an impedance within a gastroesophageal tract; and
a passive batteryless Radio Frequency Identification (RFID) circuit connected to the LC resonance circuit and the one or more electrodes, wherein the passive batteryless RFID circuit comprises a voltage regulator, a voltage multiplier connected to the voltage regulator, a transistor switch connected in parallel between the LC resonance circuit and the voltage multiplier, and an impedance to frequency converter connected to the electrodes and the voltage regulator, wherein the impedance to frequency converter controls the transistor switch, and wherein the switching frequency of the transistor switch varies with the measured impedance such that the RFID circuit transmits a frequency modulated signal using the LC resonance circuit, the frequency modulation of the transmitted signal varying between a first frequency corresponding to a non-reflux condition and a second frequency corresponding to a reflux condition, based on the measured impedance, in response to a signal received from a detector; and
wherein the sensor is adapted to be attached to the gastroesophageal tract.

2. The sensor as recited in claim 1, wherein:
the non-reflux condition comprises a substance before the substance has entered a stomach disposed on or between the electrodes; and
the reflux condition comprises a stomach acid or stomach contents disposed on or between the electrodes.

3. The sensor as recited in claim 1, wherein:
the first frequency comprises a measured frequency of between 6 k Hz and 11 kHz; and the second frequency comprises a measured frequency greater than 11 kHz.

4. The sensor as recited in claim 1, wherein:
the LC circuit comprises a parallel connected antenna and a capacitor.

5. The sensor as recited in claim 1, wherein the voltage multiplier includes a series of diodes and capacitors for energy harvesting, the impedance-to-frequency convertor converts the impedance of the electrodes to frequency-varying signals, and the sensor further comprises a modulation circuit.

6. The sensor as recited in claim 1, wherein the sensor is configured as a capsule, a tag or an implant having an overall size equal to or less than $0.5 \times l \times 3$ cm$^3$.

7. The sensor as recited in claim 3, wherein the antenna comprises at least one wire coil surrounding the electrodes.

8. The sensor as recited in claim 7, wherein the wire coil comprises at least 15 turns of a conductor having a width of 200 μm and a spacing of 50 μm in each turn.

9. The sensor as recited in claim 1, wherein the electrodes comprise at least 10 interdigitated fingers that are about 0.4 mm wide and about 5 mm long with about 0.1 mm spacing there between.

10. The sensor as recited in claim 1, wherein the passive batteryless RFID circuit uses a frequency shift keying modulation to reduce noise.

11. The sensor as recited in claim 1, wherein the electrodes are fabricated by a process comprising the steps of:
   evaporating a first conductive material on a flexible polyimide substrate;
   patterning a photoresist layer on selected portions of the first conductive material;
   electroplating the first conductive material;
   removing the photoresist layer and etching the first conductive material to form the electrodes;
   patterning an epoxy based negative resist layer; and
   electroplating a second conductive material on the electrodes.

12. A system for detecting Gastroesophageal Reflux Disease (GERD) in an animal comprising:
   a detector comprising:
      an external resonance circuit formed from an external coil,
      a power amplifier connected to the external resonance circuit,
      a radio frequency source connected to the power amplifier,
      an envelope detector connected to the power amplifier, and
      a band pass filter connected to the envelope detector; and
   one or more passive wireless gastroesophageal sensors, each sensor comprising:
      an LC (inductor capacitor) resonance circuit;
      one or more electrodes configured to measure an impedance within a gastroesophageal tract; and
      a passive batteryless Radio Frequency Identification (RFID) circuit connected to the LC resonance circuit and the one or more electrodes, wherein the passive batteryless RFID circuit comprises a voltage regulator, a voltage multiplier connected to the voltage regulator, a transistor switch connected in parallel between the LC resonance circuit and the voltage multiplier, and an impedance to frequency converter connected to the electrodes and the voltage regulator, wherein the impedance to frequency converter controls the transistor switch, and wherein the switching frequency of the transistor switch varies with the measured impedances such that the RFID circuit transmits a frequency modulated signal using the LC resonance circuit, the frequency modulation of the transmitted signal varying between a first frequency corresponding to a non-reflux condition and a second frequency corresponding to a reflux condition based on the measured impedance in response to a signal received from a detector; and
      wherein the sensor is adapted to be attached to the gastroesophageal tract.

13. The system as recited in claim 12, wherein the power amplifier is a class-E power amplifier and the envelope detector includes a diode, RC networks, and an op-amp buffer.

14. The system as recited in claim 12, wherein: the first frequency comprises a measured frequency of between 6 kHz and 11 kHz; and the second frequency comprises a measured frequency greater than 11 kHz.

15. The system as recited in claim 12, wherein:
   the LC resonance circuit comprises a parallel connected antenna and a capacitor.

16. The system as recited in claim 12, wherein the one or more sensors comprise multiple sensors implanted to detect a refluxate in multiple areas of the gastroesophageal tract of the animal.

17. The system as recited in claim 12, wherein the electrodes are fabricated by a process comprising the steps of:
   evaporating a first conductive material on a flexible polyimide substrate;
   patterning a photoresist layer on selected portions of the first conductive material;
   electroplating the first conductive material;
   removing the photoresist layer and etching the first conductive material to form the electrodes;
   patterning an epoxy based negative resist layer; and
   electroplating a second conductive material on the electrodes.

18. The system as recited in claim 12, wherein the external resonance circuit is uniquely coupled to each sensor.

19. The system as recited in claim 12, wherein the external resonance circuit is uniquely coupled to more than one of the sensors.

* * * * *

UNITED STATES PATENT AND TRADEMARK OFFICE
CERTIFICATE OF CORRECTION

PATENT NO. : 8,706,208 B2  
APPLICATION NO. : 12/054378  
DATED : April 22, 2014  
INVENTOR(S) : Chiao et al.

Page 1 of 1

It is certified that error appears in the above-identified patent and that said Letters Patent is hereby corrected as shown below:

Title Page, Item (75) Inventor is corrected to read:  
-- Jung-Chih Chiao, Grand Prairie, TX (US);  
    Thermpon, Ativanichayaphong, Valencia, CA (US);  
    Shou-Jiang Tang, Jackson, MS (US);  
    Harry F. Tibbals, Dallas, TX (US);  
    Stuart Spechler, Dallas, TX (US) --.

Signed and Sealed this  
Twelfth Day of May, 2015

Michelle K. Lee  
*Director of the United States Patent and Trademark Office*